(12) United States Patent
Iavarone et al.

(10) Patent No.: US 7,816,089 B2
(45) Date of Patent: Oct. 19, 2010

(54) METHODS FOR DIAGNOSING AND TREATING PEDIATRIC NEOPLASMS

(76) Inventors: Antonio Iavarone, 245 E. 72nd St., Apt. 14A, New York, NY (US) 10021; Anna Lasorella, 245 E. 72nd St., Apt. 14A, New York, NY (US) 10021

( * ) Notice: Subject to any disclaimer, the term of this patent is extended or adjusted under 35 U.S.C. 154(b) by 327 days.

(21) Appl. No.: 11/101,164

(22) Filed: Apr. 7, 2005

(65) Prior Publication Data
US 2006/0121494 A1 Jun. 8, 2006

Related U.S. Application Data

(63) Continuation of application No. 10/025,170, filed on Dec. 18, 2001, now abandoned.

(60) Provisional application No. 60/257,847, filed on Dec. 21, 2000.

(51) Int. Cl.
  G01N 33/53 (2006.01)
  G01N 33/567 (2006.01)
  G01N 33/574 (2006.01)
  C07K 16/00 (2006.01)
  C07K 16/18 (2006.01)
  C07K 16/30 (2006.01)

(52) U.S. Cl. ............ 435/7.1; 435/7.21; 435/7.23; 530/387.1; 530/387.7

(58) Field of Classification Search .............. None
See application file for complete search history.

(56) References Cited

U.S. PATENT DOCUMENTS

| 5,527,897 A | 6/1996 | Oda et al. |
| 6,127,178 A | 10/2000 | Israel et al. |
| 2002/0151681 A1 | 10/2002 | Rosen et al. |

OTHER PUBLICATIONS

Sablitzky et al. (Cell Growth & Differentiation, Dec. 1998, 9:1015-1024).*
Renné et al. (Am J. Pathol. 2006, 169: 655-664).*
Boyd (The Basic Science of Oncology, 1992, McGraw-Hill, Inc., p. 379).*
Taber's Cyclopedic Medical Dictionary (1985, F.A. Davis Company, Philadelphia, p. 274).*
Busken, C. et al, (Digestive Disease Week Abstracts and Itinerary Planner, 2003, abstract No. 850).*
Kaiser (Science, 2006, 313, p. 1370).*
Bowie et al (Science, 1990, 257:1306-1310).*
Burgess et al (J of Cell Bio. 111:2129-2138, 1990).*
Sambrook et al. (Molecular Cloning: A Laboratory Manual, 1989, p. 18.70-18.75).*
Lazar et al (Molecular and Cellular Biology, 1988, 8:1247-1252).*
Rudikoff et al, (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Biedler et al. (Cancer Research, Nov. 1973, 33:2643-2652).*
Stupack et al. (Nature, Jan. 2006, vol. 439: 95-99).*
Ren, C et al, (1998, Cancer Res., 58(6): 1285-90).*
Gingrich, JR et al. (1996, Cancer Res., 56(18): 4096-4102).*
Gebauer et al. (Genes, Chromosomes, & Cancer, 2004, 41: 297-308).*
Sato et al. (European J. Surgical Oncol. 2003 29:284-287).*
Alaminos et al. (Pediatr. Blood Cancer 2005 : 45:909-915).*
Burchill SA et al., "Circulating Neuroblastoma Cells Detected by Reverse Transcriptase Polymerase Chain Reaction for Tyrosine Hydroxylase mRNA Are an Independent Poor Prognostic Indicator in Stage 4 Neuroblastoma in Children Over 1 Year," J Clin Oncol. Mar. 15, 2001; 19(6):1795-1801.
Cotta CV et al., "The Helix-Loop-Helix Protein Id2 is Expressed Differentially and Induced by Myc in T-Cell Lymphomas," Cancer, Feb. 1, 2008; 112(3):552-61.
Fukuma, M. et al., "Upregulation of Id2, An Oncogenic Helix-Loop-Helix Protein, Is Mediated by the Chimeric EWS/ets Protein in Ewing Sarcoma," Oncogene (2003) 22, 1-9.
A. Lasorella et al., "Id2 Mediates Tumor Initiation, Proliferation, and Angiogenesis in Rb Mutant Mice," Molecular and Cellular Biology, May 2005, vol. 25, No. 9, pp. 3563-3574.
A. Lasorella et al., "Id2 is a Retinoblastoma Protein Target and Mediates Signalling by Myc Oncoproteins," Nature, Oct. 5, 2000; 407 (6804):592-8.
Nishimori, H. et al., "The Id2 Gene Is a Novel Target of Transcriptional Activation by EWS-ETS Fusion Proteins in Ewing Family Tumors," Oncogene (2002) 21, 8302-8309.
Renne, C. et al., "Aberrant Expression of ID2, a Suppressor of B-Cell-Specific Gene Expression, in Hodgkin's Lymphoma," The American Journal of Pathology, vol. 169, No. 2, Aug. 2006, 655-664.
Vandeputte DA et al, "Expression and Distribution of Id Helix-Loop-Helix Proteins in Human Astrocytic Tumors," Glia, Jun. 2002; 38(4):329-38.
Cheung, Irene Y. et al., Molecular Detection of GAGE Expression in Peripheral Blood and Bone Marrow: Utility as a Tumor Marker for Neuroblastoma, Clinical Cancer Research, vol. 3, pp. 821-826, May 1997.
Corrias, Maria Valeria et al., Detection of Neuroblastoma Cells in Bone Marrow and Peripheral Blood by Different Techniques: Accuracy and Relationship with Clinical Features of Patients, Clinical Cancer Research, vol. 10, pp. 7978-7985, Dec. 1, 2004.
Alevizopoulos et al., Cyclin E and c-Myc Promote Cell Proliferation in the Presence of p16INK4a and of Hypophosphorylated Retinoblastoma Family Proteins, *EMBO J.*, 16:5322-33, 1997.
Biggs et al., A Human Id-Like Helix-Loop-Helix Protein Expressed During Early Development, *Proc. Natl. Acad. Sci. USA*, 89:1512-16, 1992.

(Continued)

*Primary Examiner*—Peter J Reddig
(74) *Attorney, Agent, or Firm*—Virtual Law Partners LLP; David A. Roise

(57) ABSTRACT

The present invention provides a method for determining whether a subject has a pediatric neoplasm. The present invention further provides a method for assessing the efficacy of therapy to treat a pediatric neoplasm in a subject who has undergone or is undergoing treatment for a pediatric neoplasm. In addition, the present invention provides a method for assessing the prognosis of a subject who has a pediatric neoplasm. Finally, the present invention provides a method for treating a pediatric neoplasm in a subject in need of treatment thereof.

14 Claims, 17 Drawing Sheets

OTHER PUBLICATIONS

Bordow et al., Prognostic Significance of MYCN Oncogene Expression in Childhood Neuroblastoma, *J. Clin. Oncol.*, 16:3286-94, 1998.
Boyd et al., c-Myc target gene specificity is determined by a post-DNA-binding mechanism. Proc. Natl Acad. Sci. USA, 95:13887-92, 1998.
Brodeur et al., Neuroblastoma, Effect of Genetic Factors on Prognosis and Treatment, *Cancer*, 70:1685-94, 1992.
Cance et al., Altered Exprssion of the Retinoblastoma Gene Product in Human Sarcomas, *N. Engl. J. Med.*, 323:1457-62, 1990.
Chan et al., MYCN Protein Expression As a Predictor of Neuroblastoma Prognosis, *Clin. Cancer Res.*, 3:1699-706, 1997.
Clarke et al., Requirement For a Functional Rb-1 Gene in Murine Development, *Nature*, 359:328-30, 1992.
Cohn et al., MYCN Expression Is Not Prognostic of Adverse Outcome in Advanced-Stage Neuroblastoma With Nonamplified MYCN, *J. Clin. Oncol.*, 18:3604-13, 2000.
Cooper et al., Expression of the Id Family Helix-Loop-Helix Regulators During Growth and Development in the Hematopoietic System, *Blood*, 89:3155-65, 1997.
Cordon-Cardo et al., Altered Expression of the Retinoblastoma Gene Product: Prognostic Indicator in Bladder Cancer, *J. Natl. Cancer Inst.*, 84:1251-56, 1992.
Dyson, N., The regulation of E2F by pRB-family proteins. Genes & Dev., 12:2245-62, 1998.
Florio et al., Id2 Promotes Apoptosis By a Novel Mechanism Independent of Dimerization to Basic Helix-Loop-Helix Factors, *Mol. Cell. Biol.*, 18:5435-44, 1998.
Goodrich and Lee, Abrogation by c-Myc of G1 Phase Arrest Induced By RB Protein But Not By p53 [published erratum: *Nature*, 360:491, 1992].
Hirning et al., A Comparative Analysis of N-myc and C-myc Expression and Cellular Proliferation in Mouse Organogenesis, *Mech. Dev.*, 33:119-25, 1991.
Hiyama et al., Immunohistochemical Analysis of N-myc Protein Expression in Neuroblastoma: Correlation With Prognosis of Patients, *J. Pediatr. Surg.*, 26:838-43, 1991.
Iavarone et al., The Helix-Loop-Helix Protein Id-2 Enhances Cell Proliferation and Binds to the Retinoblastoma Protein, *Genes Dev.*, 8:1270-84, 1994.
Iavarone and Massague, E2F and histone deacetylase mediate transforming growth factor beta repression of cdc25A during keratinocyte cell cycle arrest. Mol. Cell. Biol., 19:916-22, 1999.
Ishiguro et al., Expression of ID2 and ID3 mRNA in Human Lymphocytes, *Leuk. Res.*, 19(12):989-96, 1995.
Ishiguro et al., Id2 Expression Increases With Differentiation of Human Myeloid Cells, *Blood*, 78(12):5225-31, 1996.
Jacks et al., Effects of an Rb Mutation in the Mouse, *Nature*, 359:295-300, 1992.
Jen et al., Expression patterns of Id1, Id2, and Id3 are highly related but distinct from that of Id4 during mouse embryogenesis. Dev. Dyn., 207:235-52, 1996.
Jen et al., Each Member of the Id Gene Family Exhibits a Unique Expression Pattern in Mouse Gastrulation and Neurogenesis, *Dev. Dyn.*, 208:92-106, 1997.
Kibel, AS et al (2000, J Urol, 164(1):192-6).
Kleef et al., The Helix-Loop-Helix Protein Id2 Is Overexpressed in Human Pancreatic Cancer, *Cancer Res.*, 58(17):3769-72, 1998.
Kratzke et al., Rb and p16INK4a Expression in Resected Non-Small Cell Lung Tumors, *Cancer Res.*, 56:3415-20, 1996.
Lasorella et al., ID2 Specifically Alters Regulation of the Cell Cycle by Tumor Suppressor Proteins, *Mol. Cell. Biol.*, 16:2570-78, 1996.
Lasorella et al., Id2 Is a Retinoblastoma Protein Target and Mediates Signalling by Myc Oncoproteins, *Nature*, 407:592-98, 2000.
Lasorella et al (Cancer Research, 2002, 62:301-305).
Lee et al., Mice Deficient for Rb Are Nonviable and Show Defects in Neurogenesis and Hematopoiesis, *Nature*, 359:288-94, 1992.
Lee et al., Dual Roles of the Retinoblastoma Protein in Cell Cycle Regulation and Neuron Differentiation, *Genes Dev.*, 8:2008-21, 1994.
Lyden et al., Id1 and Id3 Are Required For Neurogenesis, Angiogenesis and Vascularization of Tumour Xenografts, *Nature*, 401:670-77, 1999.
Maris and Matthay, Molecular Biology of Neuroblastoma, *J. Clin. Oncol.*, 17:2264-79, 1999.
Martinsen and Bronner-Fraser, Neural Crest Specification Regulated by the Helix-Loop-Helix Repressor Id2, *Science*, 281:988-91, 1998.
Maruyama H. et al: Id-1 and Id-2 are overexpressed in pancreatic cancer and in dysplastic lesions in chronic pancreatitis. Amer. J of Pathology, 155:3; 815-822, 1999.
Massari and Murre, Helix-loop-helix proteins: regulators of transcription in eucaryotic organisms. Mol. Cell. Biol., 20:429-40, 2000.
Mori et al., Lactation Defect in Mice Lacking the Helix-Loop-Helix Inhibitor Id2, *Embo J.*, 19:5772-81, 2000.
Morrow et al., Overexpression of the Helix-Loop-Helix Protein Id2 Blocks T Cell Development at Multiple Stages, *Mol. Immunol.*, 36:491-503, 1999.
Mulligan and Jacks, The retinoblastoma gene family: cousins with overlapping interests. Trends Genet., 14:223-29, 1998.
Murphy et al (Mol. Cell. Biol., 2004, 2083-2090).
Neuman et al., Neuronal Expression of Regulatory Helix-Loop-Helix Factor Id2 Gene in Mouse, *Dev. Biol.*, 160:186-195, 1993.
Neuman et al., Helix-loop-helix transcription factors regulate Id2 gene promoter activity. FEBS Lett., 374:279-83, 1995.
Norton et al., Id Helix-Loop-Helix Proteins in Cell Growth and Differentiation, *Trends Cell Biol.*, 8:58-65, 1998.
Norton, J.D., ID Helix-Loop-Helix Proteins in Cell Growth, Differentiation and Tumorigenesis, *J. Cell Sci.*, 113:3897-905, 2000.
Pietenpol et al., TGF-beta 1 inhibition of c-Myc transcription and growth in keratinocytes is abrogated by viral transforming protein with pRB binding domains. Cell, 61:777-85, 1990.
Ren, C et al (1998, Cancer Res, 58(6):1285-90).
Sato et al (EJSO, 2003, 29:284-287).
Sellers and Kaelin, Role of the retinoblastoma protein in the pathogenesis of human cancer. J. Clin. Oncol., 15:3301-12, 1997.
Slack et al., A Critical Temporal Requirement for the Retinoblastoma Protein Family During Neuronal Determination, *J. Cell Biol.*, 140:1497-1509, 1998.
Toma et al., Evidence That Helix-Loop-Helix Proteins Collaborate With Retinoblastoma Tumor Suppressor Protein to Regulate Cortical Neurogenesis, *J. Neurosci.*, 20:7648-56, 2000.
Tsai et al., Mutation of E2f-1 Suppresses Apoptosis and Inappropriate S Phase Entry and Extends Survival of Rb-Deficient Mouse Embryos, *Mol. Cell*, 2:293-304, 1998.
Vandesompele et al (Oncogene, 2003, 22:456-460).
Wang et al., A Role For the Helix-Loop-Helix Protein Id2 in the Control of Oligodendrocyte Development, *Neuron*, 29:603-14, 2001.
Wang et al (Cancer Research, 2003, 1631-1635).
Weinberg, The retinoblastoma protein and cell cycle control. Cell, 81:323-30, 1995.
Yokota et al., Development of Peripheral Lymphoid Organs And Natural Killer Cells Depends on the Helix-Loop-Helix Inhibitor Id2, *Nature*, 397:702-06, 1999.
Zhau, HE (1994, J Cell Biochem, Suppl 19:208-216).
Zhu et al., Id gene expression during development and molecular cloning of the human Id-1 gene. Mol. Brain Res., 30:312-26, 1995.

* cited by examiner

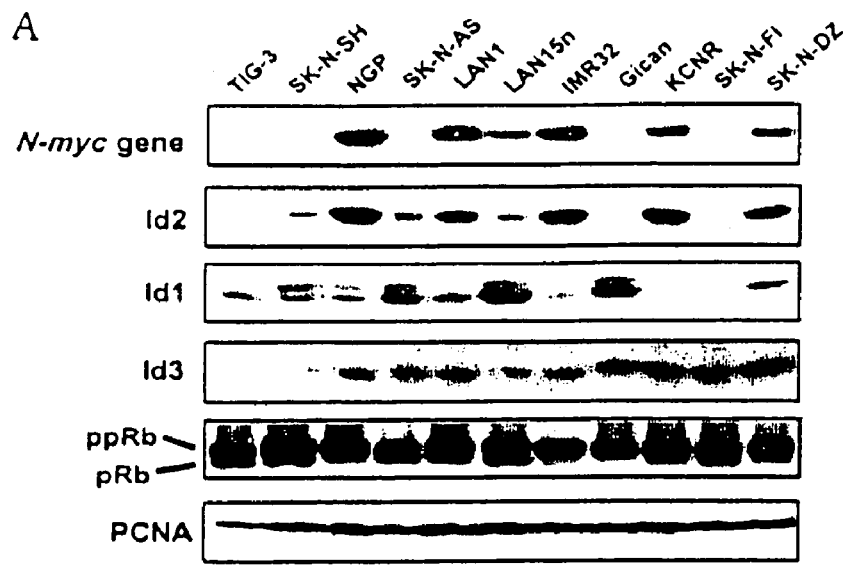
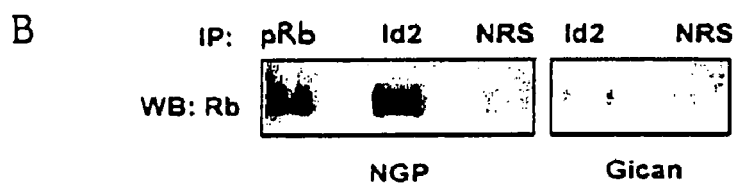
C
|  | Id2<br>pmole in 10⁶ cells | pRb<br>pmole in 10⁶ cells | Id2:pRb<br>Molar ratio |
|---|---|---|---|
| NGP | 35.2 | 5.5 | 6.5:1 |
| Gican | 1.0 | 9.1 | 0.1:1 |
FIGURE 4

Id2 antisense oligonucleotides decrease Id2 and S phase in neuroblastoma cells

NUCLEOTIDE SEQUENCE

ATGAAAGCCTTCAGTCCCGTGAGGTCCGTTAGGAAAAACAGCCTGTCGGACC
ACAGCCTGGGCATCTCCCGGAGCAAAACCCCTGTGGACGACCCGATGAGCCT
GCTATACAACATGAACGACTGCTACTCCAAGCTCAAGGAGCTGGTGCCCAGC
ATCCCCCAGAACAAGAAGGTGAGCAAGATGGAAATCCTGCAGCACCTCATCG
ACTACATCTTGGACCTGCAGATCGCCCTGGACTCGCATCCCACTATTGTCAGC
CTGCATCACCAGAGACCCGGGCAGAACCAGCGCTCCAGGACGCCGCTGACCA
CCCTCAACACGGATATCAGCATCCTGTCCTTGCAGGCTTCTGAATTCCCTTCT
GAGTTAATGTCAAATGACAGCAAAGCACTGTGTGGCTGA

AMINO-ACID SEQUENCE

MKAFSPVRSVRKNSLSDHSLGISRSKTPVDDPMSLLYNMNDCYSKLKELVPSIPQ
NKKVSKMEILQHLIDYILDLQIALDSHPTIVSLHHQRPGQNQRSRTPLTTLNTDISI
LSLQASEFPSELMSNDSKALCG*

Figure 13

METHODS FOR DIAGNOSING AND TREATING PEDIATRIC NEOPLASMS

RELATED APPLICATIONS

This application is a continuation of U.S. patent application Ser. No. 10/025,170, filed Dec. 18, 2001, now abandoned, which claims the benefit of U.S. Provisional Patent Application No. 60/257,847, filed Dec. 21, 2000, the contents of both application are hereby incorporated by reference into the subject application.

STATEMENT OF GOVERNMENT INTEREST

This invention was made with government support under NIH Grant No. RO1-CA85628-01. As such, the United States government has certain rights in this invention.

BACKGROUND OF THE INVENTION

Pediatric neoplasms are those which frequently arise in children. Examples of pediatric neoplasms include Wilms' tumor, neuroblastoma, retinoblastoma, leukemia, and tumors of the central nervous system (CNS). Common malignant pediatric tumors of the CNS include cerebellar astrocytomas and medulloblastomas, ependymomas, gliomas of the brain stem and optic nerve, germinomas, and congenital tumors. The most common metastatic tumors in children are neuroblastoma and leukemia (meningeal) (49).

Despite remarkable improvement in the survival rate of children with malignant disorders over the past two decades, cancer is still the second leading cause of death in children, after accidents (43). It has been estimated that more than 100,000 person-years of life are lost to pediatric cancer each year (44). While leukemia is the most common childhood cancer, estimates suggest that the incidences of certain other pediatric neoplasms, such as non-Hodgkin's lymphoma, neuroblastoma, glioma, primitive neuroectodermal tumor (PNET)/medulloblastoma, and other CNS tumors, have increased in recent decades (45).

Pediatric neoplasms are frequently embryonal neoplasms (i.e., neoplasms that originated during embryogenesis). Neuroblastoma, for example, is a solid malignant pediatric tumor that derives from the neural crest during development. It arises mainly in the adrenal gland, but also may arise from any portion of the extra-adrenal sympathetic chain, including the retroperitoneum and chest (49). Approximately 65% of neuroblastomas begin in the abdomen, and 15-20% begin in the thorax. The remaining 15% arise from various sites, including the neck and pelvis. Rarely, neuroblastoma can occur as a primary CNS tumor (49). Neuroblastoma is the most common extracranial tumor of childhood, and represents 10% of pediatric cancers. Approximately 75% of children with neuroblastomas are less than 5 years of age (49).

Amplification of the proto-oncogene N-myc is a common molecular finding in neuroblastoma. In approximately 30% of primary neuroblastomas, N-myc is amplified in multiple copies. N-myc amplification is associated with advanced disease and poor prognosis. Disseminated disease is also associated with poor prognosis. Common sites of dissemination include the bone, bone marrow, liver, lymph nodes, and skin (49). In approximately two-thirds of patients who have neuroblastoma, the disease is already disseminated at the time of diagnosis. Thus, there exists a need to develop strategies for earlier diagnosis.

Ultrasound and computed tomography are used to assess the nature and extent of the primary tumor in patients with neuroblastoma (49). At present, Stage I and Stage II neuroblastomas are treated by surgical excision of localized primary lesions. This treatment is successful in most cases. For Stage III and Stage IV neuroblastoma, where the disease has disseminated, therapy consists of intensive chemotherapeutic and radiation treatments. Chemotherapeutic drugs used to treat advanced disease include carboplatin, cisplatin, cyclophosphamide, doxorubicin, etoposide, and vincristine (49).

Better prognosis is indicated for children younger than one year, for children with a low stage of disease (Stage I or II), and for children in whom the tumor lacks amplification of the N-myc proto-oncogene (49). Poor prognosis is indicated for children older than one year, for children with advanced disease (Stage III or IV), and for children in whom the tumor shows amplification of N-myc. Prognosis is particularly poor for patients more than 1 year old who have an advanced stage of disease with amplification of N-myc, even with intensive treatment. Fewer than 20% of these patients survive five years post-diagnosis. Survival rates range from 30% to 40% for children with an advanced stage of disease but no N-myc amplification, and for children less than 1 year old who have an advanced stage of disease.

Retinoblastoma, another malignant pediatric tumor, arises from the immature retina (49). This pediatric neoplasm occurs in 1/15,000 to 1/30,000 live births, and represents about 2% of childhood malignancies. If diagnosed when the tumor is intraocular, more than 90% of patients can be cured. Unilateral retinoblastoma is managed by enucleation, with removal of as much of the optic nerve as possible. For those with bilateral disease, vision usually can be preserved with bilateral coagulation or unilateral enucleation and photocoagulation, cryotherapy, or radiation of the other eye. Systemic chemotherapy, such as carboplatin and etoposide, or cyclophosphamide and vincristine, may be helpful, particularly when the disease has disseminated beyond the globe (49).

Wilms' tumor, or nephroblastoma, is a malignant pediatric tumor of the kidney (49). It is composed of differing combinations of blastemal, epithelial, and stromal elements. Wilms' tumor generally presents in children under the age of 5, but sometimes may be found in older children. Prognosis depends upon the histologic appearance of the tumor, the stage at the time of diagnosis, and the age of the patient (with younger children having a more favorable prognosis). Prompt surgical exploration of potentially resectable lesions is generally carried out, along with examination of the contralateral kidney. Depending upon the stage of the disease, chemotherapy with actinomycin D and vincristine, either with or without radiation therapy, is used. Children with more advanced disease may also receive doxorubicin.

Despite the above-mentioned methods for detecting, diagnosing, and treating various pediatric neoplasms, cancer remains a significant factor in deaths of children under age 15. Successful management of pediatric neoplasms depends, in part, upon early detection of tumors. As with other cancers, a correlation exists between the tumor burden in a patient with a pediatric neoplasm, and that patient's chances of survival. Thus, the mortality from pediatric cancers can be reduced if tumors are found and treated at an early stage. Moreover, while treatment-related improvements in survival may have resulted in a decline in childhood cancer mortality (50), current treatment protocols can be invasive (surgery) or can produce deleterious side-effects (chemotherapy and radiation). Side-effects are a particular concern in the treatment of pediatric neoplasms because children are still growing: chemotherapy and radiation can interfere with growth, and the consequences can be very serious. Accordingly, it is clear that alternative strategies for diagnosis and treatment of pediatric neoplasms are still needed in order to achieve earlier diagnosis, improve survival in children with cancer, and ease the negative effects of therapy.

The Id proteins are helix-loop-helix transcription factors that have been implicated in the control of cell differentiation (1). In addition to this role in differentiation, Id proteins also have been implicated in cell-cycle control. In particular, the role of Id proteins as positive regulators of cell-cycle progression has been firmly established for one member of the Id family, Id2 (1, 3, 4). Only Id2, and not the other members of the Id-protein family (Id1 and Id3), is able to disrupt the antiproliferative effects of tumor-suppressor proteins of the Rb family (i.e., the 'pocket' proteins: Rb, p107, and p130), thereby allowing cell-cycle progression (3, 4).

It is known that Id2 mRNA is overexpressed in neoplastic cells that give rise to pancreatic cancer (46). It has also been shown that Id2 mRNA expression is prominent in certain leukemias (47, 48). However, prior to the present invention, it was not known that Id2 protein is highly expressed in cells of neuroblastomas and other solid pediatric tumors. Moreover, prior to the present invention, it was not known that Id2 mediates signaling by Myc oncoproteins, such that inhibition of Id2 in solid pediatric tumors has an antiproliferative effect.

SUMMARY OF THE INVENTION

The present invention is based upon the discovery that Id2 is expressed at significantly high levels in tumors of subjects who have neuroblastoma, and the discovery that inhibition of Id2 interrupts the Myc-Id2 transcription pathway and has an antiproliferative effect. These discoveries have broad implications in the diagnosis, monitoring, and treatment of neuroblastomas and other pediatric neoplasms.

Accordingly, it is an object of the present invention to provide a method for determining whether a subject has a pediatric neoplasm, by assaying a diagnostic sample of the subject for Id2 expression, wherein detection of Id2 expression is diagnostic of a pediatric neoplasm.

It is also an object of the present invention to provide a method for assessing the efficacy of therapy to treat a pediatric neoplasm in a subject who has undergone or is undergoing treatment for a pediatric neoplasm, by assaying a diagnostic sample of the subject for Id2 expression, wherein detection of Id2 expression in the diagnostic sample is indicative of a need to continue therapy to treat the pediatric neoplasm, and an absence of Id2 expression in the diagnostic sample is indicative of successful therapy.

It is a further object of the present invention to provide a method for assessing the prognosis of a subject who has a pediatric neoplasm, by assaying a diagnostic sample of the subject for Id2 expression, wherein the subject's prognosis improves with a decrease in Id2 expression in the diagnostic sample, the subject's prognosis worsens with an increase in Id2 expression in the diagnostic sample, the subject's prognosis is favorable at low levels of Id2 expression in the diagnostic sample, and the subject's prognosis is unfavorable at high levels of Id2 expression in the diagnostic sample.

Finally, it is an object of the present invention to provide a method for treating a pediatric neoplasm in a subject in need of treatment thereof, by inhibiting Id2.

Additional objects of the present invention will be apparent in view of the description which follows.

BRIEF DESCRIPTION OF THE FIGURES

FIGS. 4A-4C show Id2 expression in neuroblastoma cell lines. FIG. 4A illustrates a Southern blot for N-myc and a Western blot for Id2, Id1, Id3, Rb, and PCNA from ten exponentially-growing neuroblastoma cell lines and TIG-3 fibroblasts. FIG. 4B depicts immunoprecipitations from cell lysates of NGP cells, which have amplified N-myc, and Gican cells, which do not. Immunoprecipitation (IP) used anti-Id2 antibodies or normal rabbit serum (NRS), and was followed by Western blot (WB) for Rb. One-fifth of NGP lysates used in anti-Id2 and NRS IP was quantitatively immunoprecipitated with the anti-hypophosphorylated Rb antibody G99-549 (pRb). FIG. 4C shows molar amounts of Id2 and hypophosphorylated Rb in NGP and Gican. pRb: hypophosphorylated Rb; ppRb: hyperphosphorylated Rb FIG. 5A illustrates an N-Myc Western blot with lysates from NIH-3T3 cells infected with pBabe-puro (lane 1) or pBabe-puroN-mycER retroviruses (lane 2). FIG. 5B: NIH-3T3 cells containing N-myc-ER were starved of serum (−4-OHT), then treated with 4-hydroxytamoxifen (4-OHT) for 12 h (+4-OHT). Cell-cycle progression was analyzed by flow cytometry. FIG. 5C: After 4-OHT treatment for the indicated times, total RNA was analyzed by Northern blot for Id2 and GAPDH. FIG. 5D: Lysates from N-myc-ER-containing cells, either untreated (−) or treated with 4-OHT (+), were analyzed by Western blot for Id2 and Rb.

FIG. 6A shows a Western blot from serum-starved TIG-3 cells that were re-stimulated by serum for the indicated times. FIG. 6B illustrates a Northern blot of wild-type and p15$^{-/-}$ mouse embryo fibroblasts (MEFs) left untreated (−) or treated with TGF-β (+) for 8 h. FIG. 6C depicts a Western blot of Mv1Lu mink lung epithelial cells expressing inducible c-Myc treated with (+tet) or without tetracycline (−tet), followed by treatment with TGF-β for the indicated times. Densitometric quantification of Id2 is shown on the right. FIG. 6D portrays a Northern blot of total RNA from serum-starved Rat-1 cells containing c-Myc-ER treated with 4-OHT for the indicated times. FIG. 6E shows c-Myc and Id2 proteins in MEFs infected with LZRS-GFP (lane 1) or LZRS-c-Myc-GFP (lane 2) retroviruses.

FIG. 7A shows Id2 promoter-luciferase constructs. Arrows indicate primers of PCR reactions in a chromatin immunoprecipitation assay.

FIGS. 8A and 8B: MEFs of the indicated genotypes were infected with pBabe-puroc-MycER (8A) or pBabe-puroN-mycER (8B), and starved of serum. Where indicated, Id2$^{-/-}$ MEFs were infected first with LZRS-Id2-GFP retrovirus, and subsequently with pBabe-puroMycER retrovirus. Myc-ER fusion proteins were activated by 4-OHT, and cells were assayed for 5-deoxybromouridine (BrdU) incorporation. Black bars show untreated MEFs, and hatched bars show 4-OHT-treated MEFs. FIGS. 8C and 8E: Cells infected with LZRS-GFP (black bars) or LZRS-c-Myc-GFP retrovirus (hatched bars) were serum-starved and assayed for BrdU incorporation (8C) and apoptosis (8E). FIG. 8D illustrates a transformation assay. MEFs were infected with retroviruses encoding the indicated proteins, and transformed foci were stained with Giemsa after 12 days. These data are typical of several independent experiments.

FIG. 13 depicts the nucleotide sequence (SEQ ID NO:1) and corresponding amino acid sequence (SEQ ID NO:2) for Id2.

Figure 1:
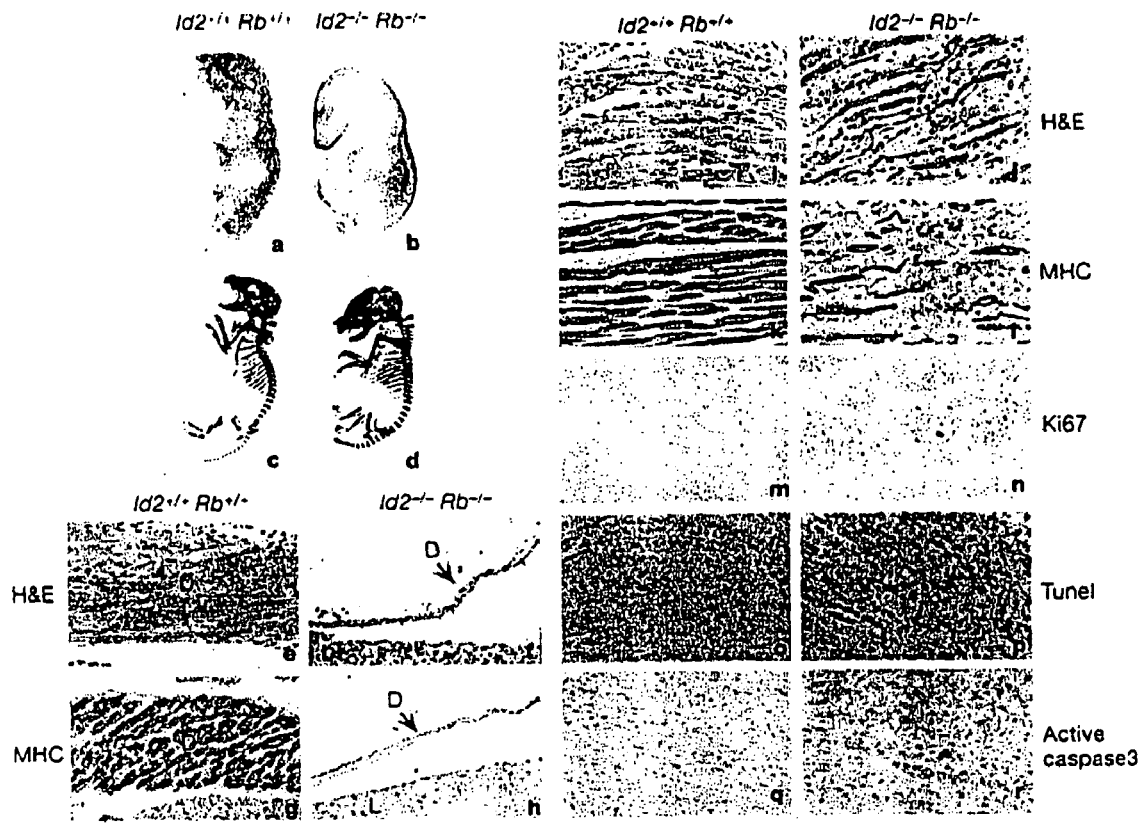
FIG. 1 illustrates abnormal myogenesis in Id2$^{-/-}$ Rb$^{-/-}$ neonates. Panels a-d show that double-mutant mice displayed altered posture at birth (hunchback). Diaphragms (panels e-h) and axial muscles (panels i-r) were stained with hematoxylin and eosin (H&E) (panels e-f, i-j), immunostained with myosin heavy chain (MHC) (panels g-h, k-l) and Ki67 (panels m-n), analyzed by Tunel assay (panels o-p), and immunostained with active caspase-3 (panels q-r). Sections shown in panels m-r were counterstained with hematoxylin and methyl green, respectively. arrow: the abnormal diaphragm of Id2$^{-/-}$ Rb$^{-/-}$ mice; D: diaphragm; L: liver; original magnification: ×40 (panels e-l, o-r); ×25 (panels m-n)

FBS, and counted at the indicated time points. Error bars are entirely contained within each symbol. Panel f illustrates a Western immunoblot from LAN1 cells treated for 24 h with 0.8 M mismatch (C) or Id2 antisense oligonucleotides (AS). Reduced Id2 protein levels are seen in cells treated with Id2 antisense oligonucleotides. A Western immunoblot for cdk2 is shown as a control for loading. Panel g illustrates that BrdU incorporation is inhibited in LAN1 expressing lower amounts of Id2. As panel h shows, LAN1 cells were treated with Id2 antisense oligonucleotides (as in panel f), and plated in soft agar. The number of colonies in triplicate wells was scored after 14 days. Data depicted in panels f-h are representative of independent experiments.

DETAILED DESCRIPTION OF THE INVENTION

The present invention provides a method for determining whether a subject has a pediatric neoplasm. As used herein, the "subject" is a mammal, including, without limitation, a cow, dog, human, monkey, mouse, pig, or rat, but is preferably a human. More preferably, the subject is a child. The method of the present invention comprises assaying a diagnostic sample of the subject for expression of Id2, wherein detection of Id2 expression is diagnostic of a pediatric neoplasm.

In mammalian cells, Id proteins coordinate proliferation and differentiation. Id proteins regulate differentiation through the sequestration of basic helix-loop-helix (bHLH) transcription factors, and the consequent inhibition of their ability to bind DNA. Id2 is a dominant-negative antagonist of bHLH transcription factors and proteins of the retinoblastoma (Rb) family. Unless otherwise indicated, "Id2" includes both an Id2 protein and an "Id2 analogue". As used herein, the "Id2 protein" has the amino acid sequence set forth in FIG. 13. An "Id2 analogue", as used herein, is a functional variant of the Id2 protein, having Id2 biological activity, that has 60% or greater (preferably, 70% or greater) amino-acid-sequence homology with the Id2 protein. An "Id2 analogue" includes a variant of the Id2 protein that has a homologous three-dimensional conformation. As further used herein, the term "Id2 biological activity" refers to the activity of a protein or peptide that demonstrates an ability to associate physically with active, hypophosphorylated forms of tumor-suppressor proteins of the Rb family (Rb, p107, and p130) (i.e., binding of approximately two fold, or, more preferably, approximately five fold, above the background binding of a negative control), and/or an ability to stimulate growth or act as an effector of Myc oncoproteins in neuroblastoma cells, as described herein. Id2 and Id2 analogues may be produced synthetically or recombinantly, or may be isolated from native cells. Id2 is preferably produced recombinantly, using conventional techniques and cDNA encoding Id2 (FIG. 13).

The method of the present invention may be used to determine whether a subject has a pediatric neoplasm, thereby permitting the diagnosis of such a neoplasm in the subject. As used herein, "a pediatric neoplasm" includes, without limitation, morphological irregularities in cells in tissue of a child, as well as pathologic proliferation of cells in tissue of a child, as compared with normal proliferation in the same type of tissue. Furthermore, a pediatric neoplasm includes an embryonal neoplasm (i.e., a neoplasm that originated during embryogenesis).

As used herein, a "neoplasm" is defined herein to mean any new and abnormal growth, particularly a new growth of tissue, in which the growth of cells is uncontrolled and progressive. A neoplasm results from "neoplasia", which refers to the uncontrolled and progressive multiplication of tumor cells, under conditions that would not elicit, or would cause cessation of, multiplication of normal cells. Neoplasms include benign tumors and malignant tumors (e.g., neuroblastomas) that are either invasive or noninvasive. Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of tumor cells having the unique trait of loss of normal controls, resulting in unregulated growth, lack of differentiation, local tissue invasion, and/or metastasis. Examples of pediatric neoplasms include, without limitation, brain tumors (e.g., glioma and medulloblastoma); Ewing's sarcoma and peripheral neuroectodermal tumors (PNET); germ-cell tumors; leukemia; neuroblastoma (i.e., a pediatric tumor derived from the neural crest during embryogenesis); retinoblastoma; rhabdomyosarcoma, osteosarcoma, and soft-tissue sarcomas; and Wilms' tumor. In one embodiment of the present invention, the pediatric neoplasm is a neuroblastoma. Preferably, the pediatric neoplasm of the present invention is a solid tumor.

According to the method of the present invention, the diagnostic sample of a subject may be assayed in vitro or in vivo. In accordance with the present invention, where the assay is performed in vitro, a diagnostic sample from the subject may be removed using standard procedures. The diagnostic sample may be tissue, particularly any bone, brain tissue, kidney tissue, muscle tissue, nervous tissue, retinal tissue, or soft tissue, which may be removed by standard biopsy. In addition, the diagnostic sample may be a bodily fluid, including cerebrospinal fluid, pericardial fluid, peritoneal fluid, saliva, serum, and urine. Furthermore, the diagnostic sample taken from the subject or patient may be, for example, any tissue known to have a pediatric neoplasm, any tissue suspected of having a pediatric neoplasm, or any tissue believed not to have a pediatric neoplasm.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody to Id2), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, a pediatric neoplasm in a subject may be diagnosed by assaying a diagnostic sample of the subject for expression of Id2. Because Id2 is generally not expressed in cells of healthy, nondiseased subjects (i.e., those who do not have a pediatric neoplasm), detection of Id2 expression in a diagnostic sample of a subject is diagnostic of a pediatric neoplasm. As used herein, "expression" means the transcription of the Id2 gene into at least one mRNA transcript, or the translation of at least one mRNA into an Id2 protein, as defined above. Accordingly, a diagnostic sample may be assayed for Id2 expression by assaying for Id2 protein (as defined above), cDNA, or mRNA. The appropriate form of Id2 will be apparent based on the particular techniques discussed herein.

In accordance with the method of the present invention, a diagnostic sample of a subject may be assayed for Id2 expression, and Id2 expression may be detected in a diagnostic sample, using assays and detection methods readily determined from the known art, including, without limitation, immunological techniques, hybridization analysis, fluorescence imaging techniques, and/or radiation detection. For example, according to the method of the present invention, a diagnostic sample of the subject may be assayed for Id2 expression using an agent reactive with Id2. As used herein, "reactive" means the agent has affinity for, binds to, or is directed against Id2. As further used herein, an "agent" shall include a protein, polypeptide, peptide, nucleic acid (including DNA or RNA), antibody, Fab fragment, F(ab')$_2$ fragment, molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. Preferably, the agent of the present invention is labeled with a detectable marker.

In one embodiment of the present invention, the agent reactive with Id2 is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified Id2. Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker. Labeling of an antibody may be accomplished using one of a variety of labeling techniques, including peroxidase, chemiluminescent labels known in the art, and radioactive labels known in the art. The detectable marker of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker may be a radioactive marker, including, for example, a radioisotope. The radioisotope may be any isotope that emits detectable radiation, such as $^{35}$S, $^{32}$P, or $^3$H. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody labeled with a detectable marker.

Where the agent of the present invention is an antibody reactive with Id2, a diagnostic sample taken from the subject may be purified by passage through an affinity column which contains Id2 antibody as a ligand attached to a solid support such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The Id2 antibody may be further attached to the solid support through a spacer molecule, if desired. Appropriate binding conditions (e.g., temperature, pH, and salt concentration) may be readily determined by the skilled artisan. In a preferred embodiment, the Id2 antibody is attached to a sepharose column, such as Sepharose 4B.

Where the agent is an antibody, a diagnostic sample of the subject may be assayed for Id2 expression using binding studies that utilize one or more antibodies immunoreactive with Id2, along with standard immunological detection techniques. For example, the Id2 protein eluted from the affinity column may be subjected to an ELISA assay, Western blot analysis, flow cytometry, or any other immunostaining method employing an antigen-antibody interaction. Preferably, the diagnostic sample is assayed for Id2 expression using Western blotting.

Alternatively, a diagnostic sample of a subject may be assayed for Id2 expression using hybridization analysis of nucleic acid extracted from the diagnostic sample taken from the subject. According to this method of the present invention, the hybridization analysis may be conducted using Northern blot analysis of mRNA. This method also may be conducted by performing a Southern blot analysis of DNA using one or more nucleic acid probes which hybridize to nucleic acid encoding Id2. The nucleic acid probes may be prepared by a variety of techniques known to those skilled in the art, including, without limitation, the following: restriction enzyme digestion of Id2 nucleic acid; and automated synthesis of oligonucleotides having sequences which correspond to selected portions of the nucleotide sequence of the Id2 nucleic acid, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the Id2 nucleic acid. The Id2 nucleic acid used in the probes may be derived from mammalian Id2. The nucleotide sequence for human Id2 is known (42). Using this sequence as a probe, the skilled artisan could readily clone corresponding Id2 cDNA from other species. In addition, the nucleic acid probes of the present invention may be labeled with one or more detectable markers. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as $^{35}$S, $^{32}$P, or $^3$H, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the Id2 nucleic acid, also may be used to assay a diagnostic sample for Id2 expression, using, for example, PCR or RT-PCR.

The detection of Id2 expression in the method of the present invention may be followed by an assay to measure or quantify the extent of Id2 expression in a diagnostic sample of a subject. Such assays are well known to one of skill in the art, and may include immunohistochemistry/immunocytochemistry, flow cytometry, mass spectroscopy, Western blot analysis, or an ELISA for measuring amounts of Id2 protein. For example, to use an immunohistochemistry assay, histological (paraffin-embedded) sections of tissue may be placed on slides, and then incubated with an antibody against Id2. The slides then may be incubated with a second antibody (against the primary antibody), which is tagged to a dye or other calorimetric system (e.g., a fluorochrome, a radioactive agent, or an agent having high electron-scanning capacity), to permit visualization of Id2 present in the sections.

It is contemplated that the diagnostic sample in the present invention frequently will be assayed for Id2 expression not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for Id2 expression.

It is also within the confines of the present invention to use detected levels of Id2 expression in an assayed diagnostic sample as a clinical or pathologic staging tool. For example, as disclosed herein, Id2 levels detected in most diagnostic samples taken from patients who had Stage I or Stage II primary neuroblastomas were significantly lower than those detected in most diagnostic samples taken from patients with Stage III or Stage IV primary neuroblastomas. Accordingly, detected levels of Id2 expression in an assayed diagnostic sample may be used to determine the grade or stage of the pediatric neoplasm found in a bodily fluid or tissue of the subject or patient. In addition, detected levels of Id2 expression in an assayed diagnostic sample may be used to determine whether any treatment method is appropriate for a particular subject or patient who has a pediatric neoplasm, including any of the treatment methods disclosed herein.

The present invention further provides a method for assessing the efficacy of therapy to treat a pediatric neoplasm in a subject or patient who has undergone or is undergoing treatment for a pediatric neoplasm. The method of the present invention comprises assaying a diagnostic sample of the subject or patient for Id2 expression, wherein detection of Id2 expression in the diagnostic sample is indicative of a need to continue therapy to treat the pediatric neoplasm, and an absence of Id2 expression in the diagnostic sample is indicative of successful therapy. The pediatric neoplasm may be any of those described above, including a neuroblastoma and other embryonal tumors. The diagnostic sample may be a tissue or a bodily fluid, as described above. The diagnostic sample may be assayed for expression of Id2 in vitro or in vivo. In addition, the diagnostic sample may be assayed for expression of Id2 using all of the various assays and methods of detection and quantification described above. This method of the present invention provides a means for monitoring the effectiveness of therapy to treat a pediatric neoplasm by permitting the periodic assessment of levels of Id2 expression in a diagnostic sample taken from a subject or patient.

According to the method of the present invention, a diagnostic sample of a subject or patient may be assayed, and levels of Id2 expression may be assessed, at any time following the initiation of therapy to treat a pediatric neoplasm. For example, levels of Id2 expression may be assessed while the subject or patient is still undergoing treatment for a pediatric neoplasm. Where Id2 expression continues to be detected in an assayed diagnostic sample of the subject or patient, a physician may choose to continue with the subject's or patient's treatment for the pediatric neoplasm. Where levels of Id2 expression in an assayed diagnostic sample of the subject or patient decrease through successive assessments, it may be an indication that the treatment for a pediatric neoplasm is working, and that treatment doses could be decreased or even ceased. Where levels of Id2 in an assayed diagnostic sample of the subject or patient do not rapidly decrease through successive assessments, it may be an indication that the treatment for a pediatric neoplasm is not working, and that treatment doses could be increased. Where Id2 expression is no longer detected in an assayed diagnostic sample of a subject or patient, a physician may conclude that the treatment for a pediatric neoplasm has been successful, and that such treatment may cease.

It is also within the confines of the present invention to assess levels of Id2 expression following completion of the subject's or patient's treatment for a pediatric neoplasm, in order to determine whether the pediatric neoplasm has recurred in the subject or patient. Accordingly, an assessment of levels of Id2 expression in an assayed diagnostic sample may provide a convenient way to conduct follow-ups of patients with pediatric neoplasms. Furthermore, as described above, it is within the confines of the present invention to use assessed levels of Id2 expression in an assayed diagnostic sample as a clinical or pathologic staging tool, as a means of determining the extent of the pediatric neoplasm in the subject or patient, and as a means of ascertaining appropriate treatment options.

It is contemplated that the diagnostic sample of the present invention frequently will be assayed for Id2 expression not by the subject or patient, nor by his/her consulting physician, but by a laboratory technician or other clinician. Accordingly, this method of the present invention further comprises providing to a subject's or patient's consulting physician a report of the results obtained upon assaying a diagnostic sample of the subject or patient for Id2 expression.

A correlation exists, in general, between tumor burden and the survival of a patient who has cancer. The mortality from cancer can be significantly reduced if tumors are found and treated at an early stage. As disclosed herein, Id2 levels detected in most diagnostic samples taken from patients who had Stage I or Stage II primary neuroblastomas (favorable prognosis) were significantly lower than those detected in most diagnostic samples taken from patients with Stage III or Stage IV primary neuroblastomas (unfavorable prognosis). Accordingly, the overexpression of Id2 correlates with the staging of the neuroblastoma and the prognosis of the patient.

In view of the foregoing, it is also contemplated in the present invention that assaying a diagnostic sample for Id2 expression may be a useful means of providing information concerning the prognosis of a subject or patient who has a pediatric neoplasm. Accordingly, the present invention further provides a method for assessing the prognosis of a subject who has a pediatric neoplasm, comprising assaying a diagnostic sample of the subject for Id2 expression, wherein the subject's prognosis improves with a decrease in Id2 expression in the diagnostic sample of the subject, the subject's prognosis worsens with an increase in Id2 expression in the diagnostic sample, the subject's prognosis is favorable at low levels of Id2 expression in the diagnostic sample, and the subject's prognosis is unfavorable at high levels of Id2 expression in the diagnostic sample.

In accordance with the method of the present invention, the pediatric neoplasm may be any of those described above, including neuroblastoma and other embryonal tumors. The diagnostic sample may be a tissue or a bodily fluid, as described above. The diagnostic sample may be assayed in vitro or in vivo. In addition, the diagnostic sample may be assayed using all of the various assays and detection and quantification methods described above. This method of the present invention provides a means for determining the prognosis of a subject or patient diagnosed with a pediatric neoplasm based upon the level of Id2 expression in an assayed diagnostic sample of the subject or patient.

According to the method of the present invention, a diagnostic sample of a subject or patient may be assayed, and levels of Id2 expression may be assessed, at any time during or following the diagnosis of a pediatric neoplasm in the subject or patient. For example, levels of Id2 expression in an assayed diagnostic sample may be assessed before the subject or patient undergoes treatment for a pediatric neoplasm, in order to determine the subject's or patient's initial prognosis. Additionally, levels of Id2 expression in an assayed diagnostic sample may be assessed while the subject or patient is undergoing treatment for a pediatric neoplasm, in order to determine whether the subject's or patient's prognosis has become more or less favorable.

Where levels of Id2 expression detected in an assayed diagnostic sample of the subject or patient are, or continue to remain, significantly high, a physician may conclude that the subject's or patient's prognosis is unfavorable. Where levels of Id2 expression in an assayed diagnostic sample of the subject or patient decrease through successive assessments, it may be an indication that the subject's or patient's prognosis is improving. Where levels of Id2 in an assayed diagnostic sample of the subject or patient do not decrease significantly through successive assessments, it may be an indication that the subject's or patient's prognosis is not improving. Where Id2 expression is low, or is no longer detected in an assayed diagnostic sample of the subject or patient, a physician may conclude that the subject's or patient's prognosis is favorable.

It is contemplated that the diagnostic sample of the present invention frequently will be assayed for Id2 expression not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for Id2 expression.

The discovery that Id2 can be detected in the tumors of subjects suffering from pediatric neoplasms provides a means of identifying patients with pediatric neoplasms, and presents the potential for commercial application in the form of a test for the diagnosis of pediatric neoplasms. The development of such a test could provide general screening procedures. Such procedures can assist in the early detection and diagnosis of such cancers, and can provide a method for the follow-up of patients in whom Id2 expression has been detected. Accordingly, the present invention further provides a kit for use as an assay of pediatric neoplasms, comprising an agent reactive with Id2. The agent may be any of those described above, and may be used in any of the above-described assays or methods for detecting or quantifying Id2 expression.

The present invention is also directed to a method for treating a pediatric neoplasm in a subject in need of treatment thereof. As used herein, a "subject" is a mammal, including, without limitation, a cow, dog, human, monkey, mouse, pig, or rat, as described above. Preferably, the subject is a human; more preferably, the subject is a child. Examples of pediatric neoplasms which may be treated by the method of the present invention include, without limitation, neuroblastomas and other embryonal neoplasms, as described above. Preferably, the pediatric neoplasm of the present invention is a neuroblastoma.

The method of the present invention comprises inhibiting Id2. Id2 may be inhibited in a subject by disabling, disrupting, or inactivating the function of Id2 in a pediatric neoplasm in the subject, or by diminishing the amount of Id2 in a pediatric neoplasm in the subject. Furthermore, Id2 may be inhibited by targeting Id2 directly, or by targeting Myc in the Myc-Id2 transcriptional pathway disclosed herein. Id2 inhibitors provide novel and valuable tools for treating pediatric neoplasms. Because Id2 is generally not expressed in nondiseased subjects, inhibition of Id2 should have a therapeutic effect without resulting in harmful or deleterious side-effects which frequently accompany therapy using other antineoplastic drugs or radiation.

In one embodiment of the present invention, Id2 is inhibited by administering an Id2 inhibitor to a subject who has a pediatric neoplasm. As used herein, "an Id2 inhibitor" shall include a protein, polypeptide, peptide, nucleic acid (including DNA, RNA, and an antisense oligonucleotide), antibody (monoclonal and polyclonal, as described above), Fab fragment (as described above), F(ab')$_2$ fragment (as described above), molecule, compound, antibiotic, drug, and any combinations thereof, and may be an agent reactive with Id2, as defined above. Additionally, the Id2 inhibitor may be an oligonucleotide antisense to Id2, as disclosed herein.

Oligonucleotides antisense to Id2 may be designed based on the nucleotide sequence of Id2 (FIG. 13). For example, a partial sequence of the Id2 nucleotide sequence (generally, 18-20 base pairs), or a variation sequence thereof, may be selected for the design of an antisense oligonucleotide. This portion of the Id2 nucleotide sequence may be within the 5' domain. A nucleotide sequence complementary to the selected partial sequence of the Id2 gene, or the selected variation sequence, then may be chemically synthesized using one of a variety of techniques known to those skilled in the art, including, without limitation, automated synthesis of oligonucleotides having sequences which correspond to a partial sequence of the Id2 nucleotide sequence, or a variation sequence thereof, using commercially-available oligonucleotide synthesizers, such as the Applied Biosystems Model 392 DNA/RNA synthesizer.

Once the desired antisense oligonucleotide has been prepared, its ability to inhibit Id2 then may be assayed. For example, the oligonucleotide antisense to Id2 may be contacted with tumor cells derived from a pediatric tumor cell line, and the levels of Id2 expression in the cells may be determined using standard techniques, such as Western blot analysis. Alternatively, the antisense oligonucleotide may be delivered to tumor cells derived from a pediatric tumor cell line using a liposome vehicle, then the levels of Id2 expression in the cells may be determined using standard techniques, such as Western blot analysis. Where the level of Id2 expression in tumor cells is reduced in the presence of the designed antisense oligonucleotide, it may be concluded that the oligonucleotide could be a useful Id2 inhibitor.

It is within the confines of the present invention that oligonucleotide antisense to Id2 may be linked to another agent, such as an antineoplastic drug or a ribozyme, in order to increase the effectiveness of the treatment, increase the efficacy of targeting, and/or increase the efficacy of degradation of Id2 RNA. Examples of antineoplastic drugs to which the antisense oligonucleotide may be linked include, without limitation, carboplatin, cyclophosphamide, doxorubicin, etoposide, and vincristine. Moreover, oligonucleotide antisense to Id2 may be prepared using modified bases (e.g., a phosphorothioate) to make the oligonucleotide more stable and better able to withstand degradation.

Additional Id2 inhibitors may be identified using screening procedures well known in the art. As disclosed herein, Rb prohibits the action of Id2 on its natural targets during the normal cell cycle, but oncogenic activation of the Myc-Id2 transcriptional pathway overrides the tumor-suppressor function of Rb. While it is disclosed herein that Rb binds Id2, it is not known whether, in tumor cells, Id2 disrupts the function of Rb through its binding to Rb, or Rb inactivates Id2 through its binding to Id2 but is unable to achieve this inactivation in the presence of a molar excess of Id2. Regardless of which mechanism is correct, effective Id2 inhibitors can be designed to replace Rb in its interaction with Id2. A candidate agent having the ability to bind Id2 would, as a consequence of this binding, either prevent Id2 inactivation of Rb through steric hindrance, or mimic Rb in its inactivation of Id2 and thereby reinforce the inactivation power of Rb.

In accordance with the method of the present invention, such an Rb-like agent may be identified using an in vitro assay (e.g., direct binding assay, competitive binding assay, etc.). In a direct binding assay, for example, the binding of a candidate agent to Id2 or a peptide fragment thereof may be measured directly. A candidate agent may be supplied by a peptide library, for example. Alternatively, in a competitive binding assay, standard methodologies may be used in order to assess the ability of a candidate agent to bind Id2, and thereby inhibit Rb-Id2 interaction. In such a competitive binding assay, the candidate agent competes with Rb for binding to Id2. Once bound to Id2, the candidate agent would either sterically hinder binding of Rb to Id2, thereby preventing inactivation of Rb by Id2, or function as Rb in inactivating Id2. A competitive binding assay represents a convenient way to assess inhibition of Rb-Id2 interaction, since it allows the use of crude extracts containing Id2 and Rb. A competitive binding assay may be carried out by adding Id2, or an extract containing Id2 biological activity (as defined above), to a mixture containing the candidate agent and labeled Rb, both of which are present in the mixture in known concentrations. After incubation, the Id2-agent complex may be separated from the unbound labeled Rb and unlabeled candidate agent, and counted. The concentration of the candidate agent required to inhibit 50% of the binding of the labeled Rb to Id2 ($IC_{50}$) then may be calculated.

The binding assay formats described herein employ labeled assay components. Labeling of Rb or Id2 may be accomplished using one of a variety of different chemiluminescent and radioactive labels known in the art. The label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the label may be a radioactive marker, including, for example, a radioisotope. The radioisotope may be any isotope that emits detectable radiation, including, without limitation, $^{35}S$, $^{32}P$, $^{125}I$, $^{3}H$, or $^{14}C$ Qualitative results of the above-described assays may be obtained by competitive autoradiographic-plate binding assays; alternatively, Scatchard plots may be used to generate quantitative results. The labels of the present invention may be coupled directly or indirectly to the desired component of the assay, according to methods well known in the art. The choice of label depends on a number of relevant factors, including the sensitivity required, the ease of conjugation with the compound to be labeled, stability requirements, and available instrumentation.

Both direct and competitive binding assays may be used in a variety of different configurations. In one competitive binding assay, for example, the candidate agent may compete against labeled Rb (the labeled analyte) for a specific binding site on Id2 (the capture agent) that is bound to a solid substrate, such as a column chromatography matrix or tube. Alternatively, the candidate agent may compete for a specific binding site on labeled Id2 (the labeled analyte) against wild-type Rb or a fragment thereof (the capture agent) that is bound to a solid substrate. The capture agent is bound to the solid substrate in order to effect separation of bound labeled analyte from the unbound labeled analyte. In either type of competitive binding assay, the concentration of labeled analyte that binds the capture agent bound to the solid substrate is inversely proportional to the ability of a candidate agent to compete in the binding assay. The amount of inhibition of labeled analyte by the candidate agent depends on the binding assay conditions and on the concentrations of candidate agent, labeled analyte, and capture agent that are used.

Another competitive binding assay may be conducted in a liquid phase. In this type of assay, any of a variety of techniques known in the art may be used to separate the bound labeled analyte (which may be either Rb or Id2) from the unbound labeled analyte. Following such separation, the amount of bound labeled analyte may be determined. The amount of unbound labeled analyte present in the separated sample is inversely proportional to the amount of bound labeled analyte.

In the further alternative, a homogeneous binding assay may be performed, in which a separation step is not needed. In this type of binding assay, the label on the labeled analyte (which may be either Rb or Id2) is altered by the binding of the analyte to the capture agent. This alteration in the labeled analyte results in a decrease or increase in the signal emitted by the label, so that measurement of the label at the end of the binding assay allows for detection or quantification of the analyte.

Under specified assay conditions, a candidate agent is considered to be capable of inhibiting the binding of Rb to Id2 in a competitive binding assay if the amount of binding of the labeled analyte to the capture agent is decreased by 50% or more (preferably 90% or more). Where a direct binding assay configuration is used, a candidate agent is considered to bind Id2 when the signal measured is twice the background level or higher. Furthermore, as proof of the specificity of the candidate agent identified using an Rb competitive binding assay, binding competition also may be performed using purified Id2 in the presence of washed ribosomes.

A functional assay, such as a luciferase assay, also may be used to screen for Id2 inhibitors. For example, an artificial promoter system, the E-box multimer (CANNTG) (1, 2), may be inserted in front of a reporter gene, such as luciferase. Basic helix-loop-helix (bHLH) transcription factors are the primary targets of Id2. The promoter-luciferase system may be used in the presence of bHLH transcription factors, both with and without Id2. When the bHLH transcription factors bind the E-box domain, the promoter is active and the reporter gene is transcribed. In the presence of Id2, however, the bHLH transcription factors are inhibited, and the promoter is inactive. A candidate Id2 inhibitor then may be added to the system in the presence of Id2. The promoter will be reactivated if the candidate successfully inhibits Id2, because the bHLH transcription factors will again be free to bind the E-box promoter and transcribe the reporter gene. The activity of the promoter in the presence of Id2 and the candidate Id2 inhibitor may be measured using standard techniques known to one of skill in the art.

Once the candidate agent of the present invention has been screened, and has been determined to have a suitable inhibitory effect on Id2 (i.e., it is reactive with Id2, it binds Id2, or it otherwise inactivates Id2), it may be evaluated for its effect on tumor-cell proliferation. In particular, the candidate agent may be assessed for its ability to act as an inhibitor to cell division or to otherwise function as an appropriate tumor-suppressing agent. It is expected that the Id2 inhibitor of the present invention will be useful to treat pediatric neoplasms, including those disclosed herein. Furthermore, the inventors propose that the Id2 inhibitor of the present invention might be useful for restoring proliferation control by the Rb tumor-suppressor pathway in any tumor carrying abnormal activation of the Myc-Id2 oncogenic network disclosed herein.

In the method of the present invention, an Id2 inhibitor is administered to a subject who has a pediatric neoplasm in an amount effective to treat the pediatric neoplasm in the subject. As used herein, the phrase "effective to treat the pediatric neoplasm" means effective to ameliorate or minimize the clinical impairment or symptoms resulting from the pediatric neoplasm. For example, the clinical impairment or symptoms of the pediatric neoplasm may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the maturation and proliferation of cells in the pediatric neoplasm. The amount of Id2 inhibitor effective to treat a pediatric neoplasm in a subject in need of treatment thereof will vary depending on the particular factors of each case, including the type of pediatric neoplasm, the stage of the pediatric neoplasm, the subject's weight, the severity of the subject's condition, and the method of administration. These amounts can be readily determined by the skilled artisan. In the method of the present invention, the Id2 inhibitor may be administered to a human or animal subject by known procedures, including, without limitation, oral administration, parenteral administration (e.g., epifascial, intracapsular, intracutaneous, intradermal, intramuscular, intraorbital, intraperitoneal, intraspinal, intrasternal, intravascular, intravenous, parenchymatous, or subcutaneous administration), transdermal administration, and administration by osmotic pump. Preferably, the Id2 inhibitor of the present invention is administered parenterally, by intravenous or subcutaneous injection.

For oral administration, the formulation of the Id2 inhibitor may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration, the Id2 inhibitor may be combined with a sterile aqueous solution which is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulations may be presented in unit or multi-dose containers, such as sealed ampules or vials. The formulation may be delivered by any mode of injection, including, without limitation, epifascial, intracapsular, intracutaneous, intradermal, intramuscular, intraorbital, intraperitoneal, intraspinal, intrasternal, intravascular, intravenous, parenchymatous, or subcutaneous.

For transdermal administration, the Id2 inhibitor may be combined with skin penetration enhancers, such as propylene glycol, polyethylene glycol, isopropanol, ethanol, oleic acid, N-methylpyrrolidone, and the like, which increase the permeability of the skin to the Id2 inhibitor, and permit the Id2 inhibitor to penetrate through the skin and into the bloodstream. The Id2 inhibitor/enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch. The Id2 inhibitor may be administered transdermally, at or near the site on the subject where the pediatric neoplasm is localized. Alternatively, Id2 inhibitor may be administered transdermally at a site other than the affected area, in order to achieve systemic administration.

The Id2 inhibitor of the present invention also may be released or delivered from an osmotic mini-pump or other time-release device. The release rate from an elementary osmotic mini-pump may be modulated with a microporous, fast-response gel disposed in the release orifice. An osmotic mini-pump would be useful for controlling release, or targeting delivery, of the Id2 inhibitor.

In accordance with the methods of the present invention, where the Id2 inhibitor is a protein, the Id2 inhibitor protein may be administered to a subject by introducing to the subject the Id2 inhibitor protein itself, or by introducing to the subject a nucleic acid encoding the Id2 inhibitor in a manner permitting expression of the Id2 inhibitor protein. The Id2 inhibitor protein, and other Id2 inhibitors, may be introduced to a subject by known techniques used for the introduction of proteins and other drugs, including, for example, injection and transfusion. Where a pediatric neoplasm is localized to a particular portion of the body of the subject, it may be desirable to introduce the Id2 inhibitor directly to that area by injection or by some other means (e.g., by introducing Id2 inhibitor into the blood or another body fluid). The amount of Id2 inhibitor to be used is an amount effective to treat a pediatric neoplasm in the subject, as defined above, and may be readily determined by the skilled artisan.

In the method of the present invention, where the Id2 inhibitor is a protein, the Id2 inhibitor also may be introduced to the subject by introducing into a sufficient number of cells of the subject a nucleic acid encoding the Id2 inhibitor, in a manner permitting expression of the Id2 inhibitor protein. The amount of nucleic acid encoding Id2 inhibitor is an amount that will produce Id2 inhibitor protein in an amount effective to treat a pediatric neoplasm, as defined above, in the subject. This amount may be readily determined by the skilled artisan.

Nucleic acid encoding the Id2 inhibitor, as well as any antisense oligonucleotide or other nucleotide inhibitor of Id2, may be introduced to the subject using conventional procedures known in the art, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of viruses such as retrovirus, HSV, adenovirus, adeno-associated virus, Semiliki Forest virus, cytomegalovirus, and vaccinia virus.

It is also within the confines of the present invention that a nucleic acid encoding an Id2 inhibitor may be introduced into suitable cells in vitro, using conventional procedures, to achieve expression of the Id2 inhibitor in the cells. Cells expressing the Id2 inhibitor then may be introduced into a subject to treat a pediatric neoplasm in vivo. In such an ex vivo gene therapy approach, the cells are preferably removed from the subject, subjected to DNA techniques to incorporate nucleic acid encoding the Id2 inhibitor, and then reintroduced into the subject.

It is also within the confines of the present invention that the Id2 inhibitor of the present invention may be administered to a subject who has a pediatric neoplasm, either alone or in combination with one or more antineoplastic drugs used to treat pediatric neoplasms. Examples of antineoplastic drugs with which the Id2 inhibitor may be combined include, without limitation, carboplatin, cyclophosphamide, doxorubicin, etoposide, and vincristine.

It is within the confines of the present invention that the formulation of an Id2 inhibitor may be further associated with a pharmaceutically-acceptable carrier, thereby comprising a pharmaceutical composition. The pharmaceutically-acceptable carrier must be "acceptable" in the sense of being compatible with the other ingredients of the composition, and not deleterious to the recipient thereof. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others. Formulations of the pharmaceutical composition may be conveniently presented in unit dosage.

The formulations of the present invention may be prepared by methods well-known in the pharmaceutical art. For example, the Id2 inhibitor may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the Id2 inhibitor of the present invention to a subject to treat a pediatric neoplasm. The Id2 inhibitor is provided in an amount that is effective to treat a pediatric neoplasm in the subject. That amount may be readily determined by the skilled artisan, as described above.

The present invention is described in the following Experimental Details section, which is set forth to aid in the understanding of the invention, and should not be construed to limit in any way the scope of the invention as defined in the claims which follow thereafter.

EXAMPLE 1

1. Introduction

Id proteins regulate differentiation (1) by sequestering basic helix-loop-helix (bHLH) transcription factors, thereby inhibiting their binding to DNA (2). Although all Id proteins are viewed as positive regulators of cell-cycle progression, this role has been firmly established only for one member of the Id family, Id2 (1, 3, 4). Only Id2, and not the other members of the Id-protein family (Id1 and Id3), is able to disrupt the antiproliferative effects of tumor-suppressor proteins of the Rb family (i.e., the 'pocket' proteins: Rb, p107, and p130), thereby allowing cell-cycle progression. This function correlates with the ability of Id2, but not Id1 and Id3, to associate physically with active, hypophosphorylated forms of the pocket proteins in vitro and in vivo. By inactivating Rb, Id2 is also able to abolish the function of another growth-inhibitory protein, p16, that operates upstream to Rb (3, 4).

The Rb-null phenotype is lethal by embryonic day (E) 14.5 (5-7) because of widespread proliferation, defective differentiation, and apoptosis in the nervous system and hematopoietic precursors (8, 9). Since Id2 is expressed in these cell types at the time that Rb-null embryos die (10-12), the inventors hypothesized that, if Id2 is a natural target of Rb, manifestation of the Rb-mutant phenotype might require intact Id2.

Disruption of the Rb pathway (which also includes cyclin D, cdk4/6, and p16) is a hallmark of cancer, and it is widely accepted that normal Rb function must be removed, one way or another, in all human tumors (13, 14). Therefore, the inventors set out to determine whether tumor cells deregulate Id2 to bypass the Rb pathway. Correct expression of Id2 is essential for regulating proliferation and differentiation of the neural crest; thus, neural crest precursor cells might be sensitive to inappropriate expression of Id2 (15).

In humans, neoplastic transformation of neural crest precursors during embryogenesis causes neuroblastoma (16). Interestingly, genetic alterations of Rb, cyclin D, cdk4/6, or p16 are absent in neuroblastoma (17-23). The genetic hallmark of neuroblastoma is amplification of the gene for a member of the Myc family of proto-oncogenes, N-myc. Resembling enforced expression of Id2, Myc overexpression is sufficient to bypass the Rb-p16 growth-inhibitory pathway, in spite of persistent hypophosphorylated Rb (24, 25). Consequently, Myc activation may release the pressure to mutate components of the Rb-p16 pathway during tumorigenesis (24, 26).

In this example, the inventors have intercrossed Rb and Id2 mutant mice, and have shown a genetic interaction between Rb and Id2 during development. In addition, through their analysis of the involvement of Id2 in neuroblastoma, the inventors have discovered an unexpected link between Myc oncoproteins and Id2. Activation of N-myc proto-oncogene in neuroblastoma causes an increase in Id2 to a level greater than the otherwise active, hypophosphorylated Rb in these cells. The inventors have found that this effect is the result of inappropriate activity of a transcriptional network, where Myc transcription factors increase expression of Id2 to bypass the Rb block, thereby driving progression of the cell cycle.

2. Materials and Methods

A. Mouse Strains $Id2^{+/-}$ mice on 129/Sv genetic background (37) were crossed with $Rb^{+/-}$ mice on C57BL/6×129/Sv mixed background (6), to generate $Id2^{+/-} Rb^{+/-}$ mice. These mice were subsequently intercrossed to generate founders for matings described in Table 1. Mice were genotyped routinely by polymerase chain reaction (PCR) of tail DNA as described (6, 37).

TABLE 1

| | Frequency of $Rb^{-/-}$ offspring at birth | | | |
|---|---|---|---|---|
| | Total | $Rb^{-/-}$ observed ($Rb^{-/-}$ expected) | | |
| Cross | neonates | $Id2^{-/-}$ | $Id2^{+/-}$ | $Id2^{+/+}$ |
| I. $Id2^{+/-}Rb^{+/-}$ × $Id2^{-/-}Rb^{+/-}$ | 81 | 10 (10) | 5 (10) | — |
| II. $Id2^{-/-}Rb^{+/-}$ × $Id2^{-/-}Rb^{+/-}$ | 13 | 3 (3) | — | — |
| III. $Id2^{+/+}Rb^{+/-}$ × $Id2^{+/+}Rb^{+/-}$ | 113 | — | — | 0 (28) |

Numbers represent neonates derived from 13 litters (cross I), 2 litters (cross II), and 19 litters (cross III).

B. Skeletal and Histological Analysis, Immunohistochemistry, and Blood Analysis

Alcian blue and alizarin red staining for cartilage and bones was performed as described (38). For histology, neonates were fixed in 10% formalin and embedded in paraffin, from which 4-μm serial sagittal sections were cut. Sections were stained with hematoxylin and eosin, or used for immunohistochemistry with the indicated antibodies. Apoptosis was assayed using a commercial kit for Tunel assay (Roche) and active caspase-3 immunostaining (Pharmingen). Proliferation and apoptosis in the CNS were measured in multiple sections as a fraction of Ki67 and Tunel-positive cells per unit area of tissue, respectively. Peripheral blood was drawn from tail vessels, and smears were stained with Wright-Giemsa (Sigma).

C. Immunoprecipitations, Immunoblot Analysis, and Id2/Rb Quantifications

To analyze Id2 immunoprecipitates, cells were lysed as described (28), and complexes of Id2 and pocket proteins were immunoprecipitated with polyclonal antibodies against Id2 (C-20, Santa Cruz). Hypophosphorylated Rb was precipitated with monoclonal antibody G99-549 (Pharmingen) (3). To measure the endogenous amounts of Id2 and hypophosphorylated Rb expressed by neuroblastoma cells, recombinant GST-Id2 and GST-Rb were produced in bacteria, and purified. The chemiluminescent signal of known amounts of recombinant proteins was plotted against the signal given by serial dilutions of neuroblastoma cell extracts on the same Western blot against Id2 and hypophosphorylated Rb.

D. Cell Culture

Cells were maintained in DMEM supplemented with 10% fetal bovine serum (Sigma). MEFs of the indicated genotypes were prepared from E13.5 embryos as described (39), and used within the first three passages in culture. Flow cytometry analysis was done as described (3).

To generate high-titre retroviral stocks, Phoenix producer cells were used as described (40). For infection, subconfluent MEFs or NIH-3T3 cultures were incubated at 37° C. with viral supernatants in the presence of 4 µg/ml polybrene (Sigma) for 12 h. Three rounds of infection were routinely performed to accomplish a 100% rate of infection. At the end of the last infection, the viral supernatant was diluted 1:3 with complete medium, and allowed to remain on the cells for 24 h. To activate Myc-ER fusion proteins in NIH-3T3 and MEFs, cells were treated with 250 nM 4-OHT (Sigma) after 36 h of starvation in DMEM containing 0.05% serum.

Incorporation of 5-deoxybromouridine (BrdU) was quantified by immunofluorescence analysis performed on MEFs labeled with 10 µM BrdU (Roche) for 4 h. Myc-induced apoptosis was scored by visualization of nuclear condensation and blebbing of Hoescht-stained cells, and validated by Tunel assay of representative samples. The percentage of BrdU incorporation and apoptosis was determined by counting more than 1,000 cells.

E. Id2 Promoter Analysis

A human genomic library was screened with an Id2-specific cDNA probe, and two phage clones were isolated and sequenced. A 3.0-kilobase (kb) BglI-NheI fragment was subcloned in pGL3 Basic (Promega) to generate pGId2-2750. The Id2 reporter plasmid pGId2-1330 was generated by 5' deletion of the larger promoter fragment pGId2-2750. Plasmids pGId2-EcoRI and pGId2-EcoRIm were generated by placing a 900-bp EcoRI fragment upstream of a 204-bp minimal Id2 promoter. All plasmids harbor a 35-bp region downstream of the start site. Site-specific mutagenesis was performed by a PCR-based protocol, and transfections and luciferase assays were done as described (41). Luciferase activity was normalized to the expression of pCMV-LacZ cotransfected as an internal standard. PCR primers used for chromatin immunoprecipitation assays were 5'-TCTGTTC-CACTGTGGCACGTAT-3' (sense) (SEQ ID NO: 3) and 5'-CTCGATAATGGGGAAACAGTGT-3' (antisense) (SEQ ID NO: 4). A detailed protocol for chromatin crosslinking, immunoprecipitation, and PCR has been published (31).

3. Results

A. Mutation of Id2 Rescues Rb Mutant Embryos

To test whether elimination of Id2 would affect survival and/or phenotypic defects of $Rb^{-/-}$ embryos, the inventors intercrossed $Rb^{+/-}$ animals carrying variable Id2 backgrounds ($Id2^{+/+}$, $Id2^{+/-}$, $Id2^{-/-}$) (Table 1). Intercrosses from $Id2^{+/+} Rb^{+/-}$ parents generated no $Rb^{-/-}$ pups. At E15.5, $Rb^{-/-}$ embryos were found in an advanced state of resorption, confirming that death occurred by E13.5-E14.5 (5-7). However, intercrosses between $Id2^{+/-} Rb^{+/-}$ and $Id2^{-/-} Rb^{+/-}$ parents generated 100% of expected $Id2^{-/-} Rb^{-/-}$ pups, and 50% of expected $Id2^{+/-} Rb^{-/-}$ pups. These results indicate that loss of Id2 rescued the embryonic lethality of homozygous Rb mutants in a dose-dependent manner.

The $Id2^{-/-} Rb^{-/-}$ and $Id2^{+/-} Rb^{-/-}$ mice were stillborn and phenotypically identifiable at birth because of a characteristic hunchback phenotype (FIG. 1, panels a and b). Alizarin red/alcian blue staining of skeletons revealed an abnormal curvature of the vertebral column and a deformed rib cage (FIG. 1, panels c and d). Gross morphological analysis showed dramatic reduction of skeletal muscle tissue. Histological examination and immunostaining for myosin heavy chain (MHC) in regions normally occupied by respiratory muscles showed complete absence of muscle fibers (FIG. 1, panels e-h). Therefore, loss of respiratory muscle function at birth is the most likely cause of death of Id2-Rb double-mutant mice. Histological analysis and MHC immunostaining of axial and limb regions of $Id2^{-/-} Rb^{-/-}$ pups showed that myotubes were widely dispersed, compared with the compact arrangement of muscle cells from control mice. However, expression of MHC in the residual myotubes was relatively normal (FIG. 1, panels i-l). In the absence of Id2 and Rb, myotubes were frequently positive for the proliferating antigen Ki67 (FIG. 1, panels m and n) and showed an increased rate of apoptosis, as demonstrated by Tunel assay and immunostaining for the active form of caspase-3vc (FIG. 1, panels o-r).

Figure 2:
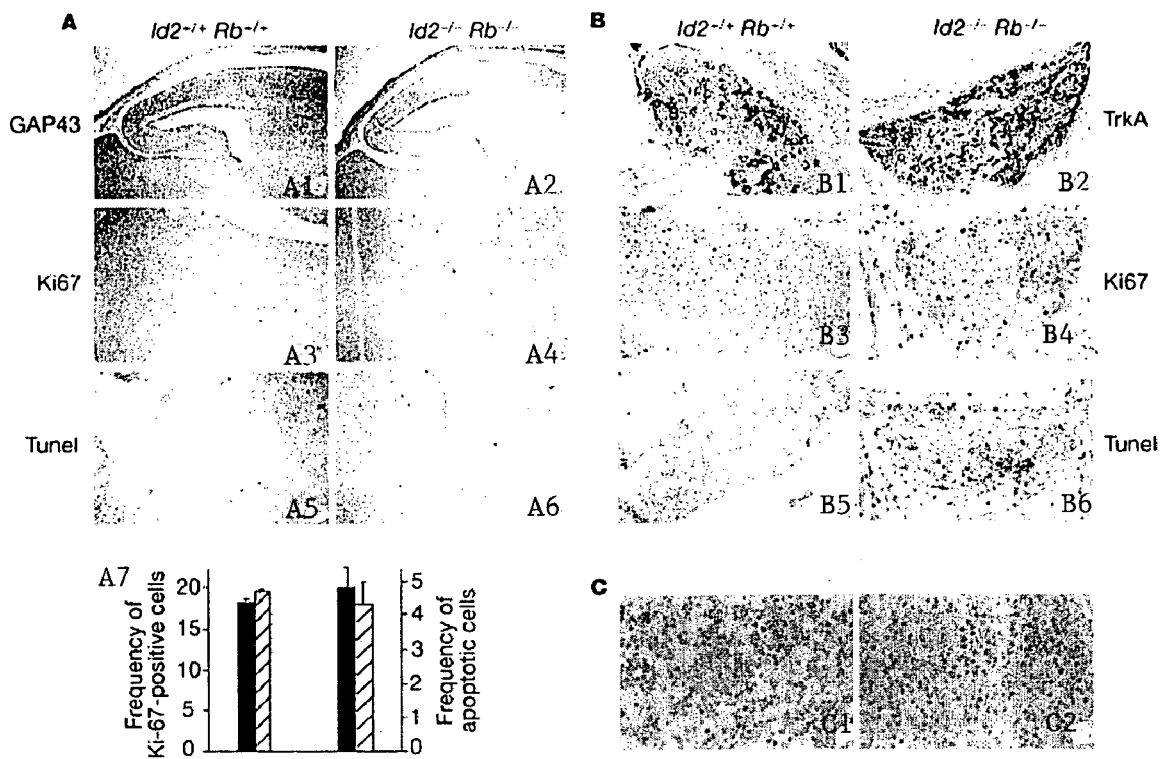
FIG. 2 portrays normal neurogenesis and erythropoiesis in Id2$^{-/-}$ Rb$^{-/-}$ neonates. Whole brain sections were immunostained with GAP43 (2A, panels A1-A2). Dorsal root ganglia were immunostained with TrkA (2B, panels B1-B2). Fourth ventricle of the brain (2A, panels A3-A6) and dorsal root ganglia (2B, panels B3-B6) were immunostained with Ki67 (2A, panels A3-A4; 2B, panels B3-B4), and analyzed by Tunel assay (2A, panels A5-A6; 2B, panels B5-B6). Sections in FIGS. 2A (panels A3-A6) and 2B (panels B3-B6) were counterstained with hematoxylin. Original magnification was ×2.5 (2A, panels A1-A2), ×10 (2A, panels A3-A6), or ×25 (2B, panels B1-B6). Peripheral blood smears are shown in FIG. 2C (panels C1-C2). Frequency of proliferating and apoptotic cells in the CNS is shown in FIG. 2A (panel A7). black bars: wild-type (n=3); hatched bars: Id2$^{-/-}$ Rb$^{-/-}$ (n=3)

The phenotypic hallmarks responsible for lethality of $Rb^{-/-}$ mice during embryogenesis, and neurological and erythroid abnormalities, were virtually absent in $Id2^{-/- Rb-/-}$ neonates (FIG. 2). In the central nervous system (CNS), immunostaining for three post-mitotic neuronal markers (GAP43, MAP2, and neurofilament 160) indicated that normal neuronal differentiation occurred in $Id2^{-/- Rb-/-}$ mice throughout development (FIG. 2A, panels A1-A2; and data not shown). $Id2^{-/-} Rb^{-/-}$ brains showed no evidence of inappropriate proliferating activity (FIG. 2A, panels A3 A4) or increased apoptosis (FIG. 2A, panels A5-A6), as determined by quantitative immunodetection of Ki67 and Tunel assay, respectively (FIG. 2A, panel A7).

In the peripheral nervous system, the inventors analyzed dorsal root ganglia (DRG) and trigeminal ganglia (FIG. 2B), two tissues that are profoundly degenerated in Rb mutant embryos (5-7, 9). Double-mutant DRG showed a near-normal expression of TrkA, a late differentiation marker of peripheral neurons that is lost in Rb mutant embryos (9, 27) (FIG. 2B, panels B1-B2). Similarly, Ki67 immunostaining (FIG. 2B, panels B3-B4) was indistinguishable from normal controls. However, the inventors saw a moderate increase in the number of apoptotic cells in $Id2^{-/-} Rb^{-/-}$ DRG (FIG. 2B, panels B5-B6). Peripheral blood smears from $Id2^{-/-} Rb^{-/-}$ mice were generally indistinguishable from those taken from normal littermates (FIG. 2C, panels C1-C2). Occasionally, the inventors found less than 1% nucleated red blood cells.

B. Regulation of Id2-Pocket Protein Complexes

Figure 3:
FIG. 3 depicts cell-cycle analysis of complexes of Id2 and pocket proteins. TIG-3 fibroblasts were synchronized in G0 by serum starvation, and stimulated to re-enter the cell cycle by addition of 20% serum. Lysates were prepared from cells harvested at 0 h, 4 h, and 14 h after serum addition, and proteins were immunoprecipitated with polyclonal anti-Id2 antibody (Anti-Id2) or normal rabbit serum (NRS). Immune complexes were analyzed by Western immunoblot for Rb, p107, p130, α-tubulin, and Id2. The same antibodies were used to detect proteins from total cellular lysates (Total). Arrow indicates migration of immunoprecipitated Id2, just below a nonspecific band (asterisk).

The inventors asked whether endogenous Id2 and pocket proteins interact in normal cells, and whether these interactions are regulated during the cell cycle. Id2 immunoprecipitates from human diploid fibroblasts (TIG-3) were analyzed for pocket proteins by Western blot (FIG. 3). The inventors prepared TIG-3 extracts from serum-starved cells (0 h; cell-cycle phase G0) and from cells stimulated by serum for 4 h (G1) and 14 h (entering S phase) (data not shown). Id2 was low but detectable in quiescent cells, and was rapidly induced by serum, with persistence of high amounts until the beginning of S phase (FIG. 3). Id2 immunoprecipitates were free of abundant cellular proteins such as α-tubulin, and pocket proteins were never precipitated by normal rabbit serum (FIG. 3; and data not shown).

Id2 bound exclusively to the hypophosphorylated forms of pocket proteins. In quiescent cells, the low amounts of Id2 were mainly associated with p130, and complexes between Id2 and p107 were undetectable in G0 and during transit through G1. The increase of Id2 4 h after addition of serum resulted in only moderate accumulation of Id2-Rb and Id2-p130 complexes. However, Id2-Rb complexes increased significantly at the beginning of S phase. At this time, the Id2-p107 interaction was also detectable, whereas Id2-p130 complexes were virtually absent.

C. Id2 Overrides Rb in Neuroblastomas with N-myc Amplification

Rb is required for normal development, and integrity of the Rb pathway is essential to prevent tumorigenesis. Hence, expression of Id2 was analyzed in ten human neuroblastoma cell lines (FIG. 4A), six of which had extra copies of the N-myc gene (NGP, LAN1, LAN 15n, IMR32, SMS-KCNR, SK-N-DZ). Five of these six had 20- to 30-fold more Id2 than did the neuroblastoma cell lines without amplification of N-myc (SK-N-SH, SK-N-AS, Gican, SK-N-FI). Expression of Id2 in neuroblastoma cell lines without N-myc amplification was comparable to TIG-3 fibroblasts (FIG. 4A). The only neuroblastoma cell line with N-myc amplification but lower expression of Id2 was LAN15n—a LAN1 derivative having fewer copies of the N-myc gene than parental cells and reduced expression of N-Myc messenger RNA. Expression of Id1 tended to be the opposite of Id2 expression, with more Id1 found in cell lines without amplification of N-myc. Id3 showed minimal differences among neuroblastoma cell lines (FIG. 4A). Southern blot analysis of p16 and cdk6, Northern blot analysis of p16, and Western blot analysis of p16, cyclin D1, and cdk4 indicated that, as reported by others (17-23), neuroblastoma cell lines carried no alterations of the known components of the Rb pathway (data not shown).

Although the degrees of Rb phosphorylation varied among neuroblastoma cells, each cell line contained detectable amounts of hypophosphorylated Rb (FIG. 4A). Next, the inventors measured the fraction of hypophosphorylated Rb recoverable as a stable complex with Id2 in neuroblastoma cell lines with or without N-myc amplification (FIG. 4B). Id2 immunoprecipitates from neuroblastoma cells contained only hypophosphorylated Rb, as shown by co-migration with Rb precipitated by an antibody specific for hypophosphorylated Rb (FIG. 4B). In NGP, a cell line with N-myc amplification, a minimum of 20% of total hypophosphorylated Rb was found in a complex with Id2. However, in Gican, a cell line without N-myc amplification, only 0.5-1% of hypophosphorylated Rb was bound to Id2. To bypass growth suppression by Rb, the molar amount of Id2 should exceed the amount of hypophosphorylated Rb in neuroblastoma cells with N-myc amplification. Accordingly, the inventors measured the Id2:Rb molar ratio in NGP and Gican (FIG. 4C). Id2 was ten-fold less than hypophosphorylated Rb in Gican. The Id2:Rb ratio was reversed in NGP, where the molar amount of Id2 exceeded hypophosphorylated Rb by a factor of 6.5. This ratio is within the range of ectopic Id2:Rb stoichiometry in Saos-2 cells, where expression of Id2 overcomes cell-cycle arrest by Rb (3).

D. Id2 is an N-Myc and c-Myc Target

Figure 5:
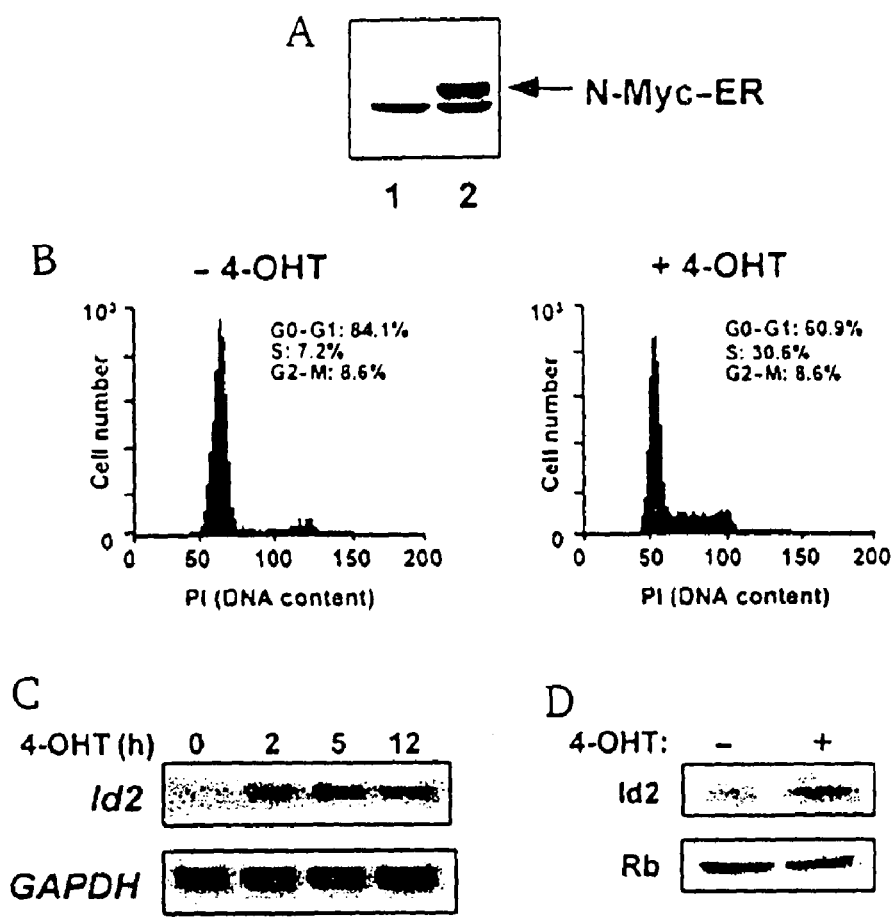
FIGS. 5A-5D show that Id2 is an N-Myc target gene.

To test whether overexpression of Id2 in neuroblastoma is the result of direct control of Id2 gene expression by N-Myc, N-myc complementary DNA was fused with estrogen receptor (ER) cDNA, and the resulting N-Myc-ER fusion protein was expressed in NIH-3T3 cells (FIG. 5A). After starving these cells of serum, activation of N-Myc-ER by 4-hydroxytamoxifen (4-OHT) caused entry into S phase (FIG. 5B). This treatment also caused a fast, strong, and sustained increase of Id2 mRNA (FIG. 5C). Id2 was not induced by 4-OHT treatment of parental NIH-3T3 or NIH-3T3 that had been infected with an empty virus (data not shown). Induction of Id2 mRNA by N-Myc-ER activation was maintained in the presence of cyclohexamide, and resulted in rapid accumulation of Id2 protein with no detectable change in abundance or phosphorylation of Rb (FIG. 5D).

Figure 6:
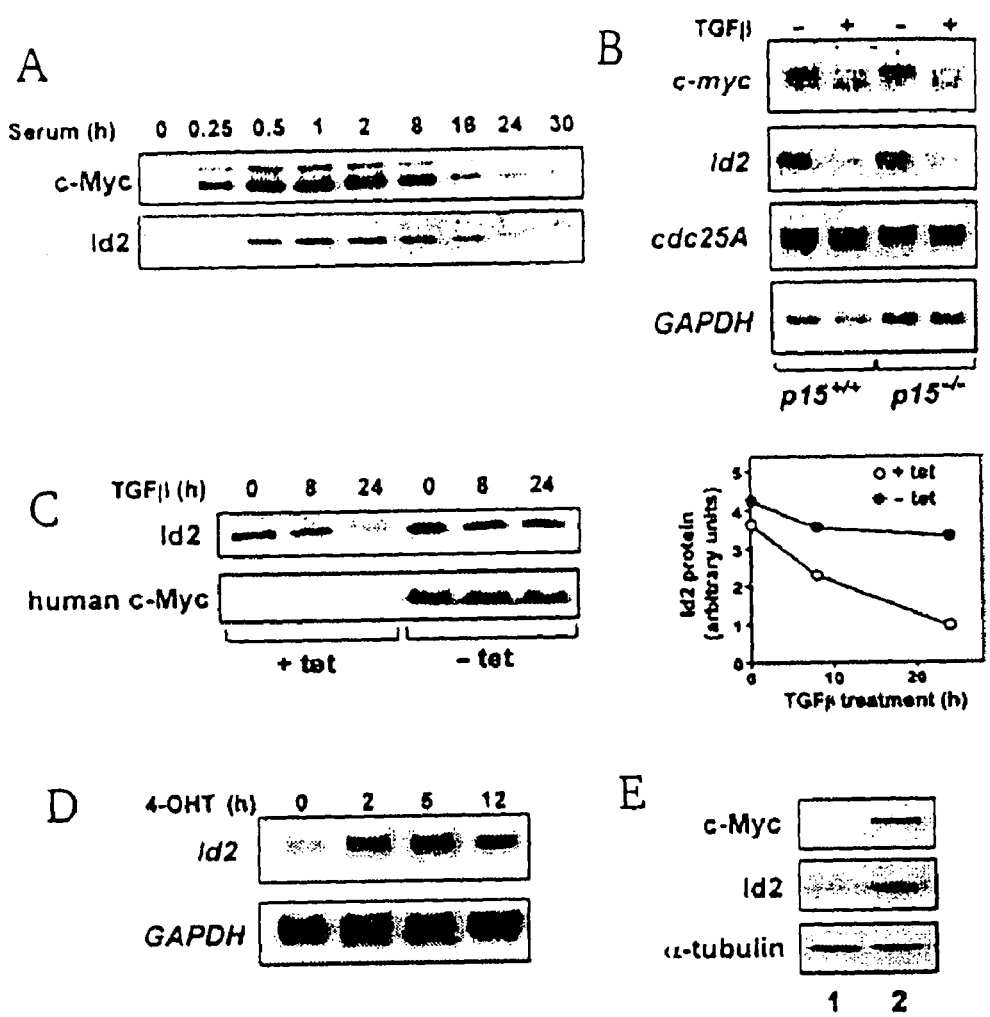
FIGS. 6A-6E demonstrate that Id2 is a c-Myc target gene.

The inventors sought to determine whether targeting Id2 expression is a common attribute of Myc family members. First, the inventors asked whether expression of c-Myc and expression of Id2 were correlated during the proliferative response of normal human fibroblasts to serum. c-Myc was rapidly induced by serum (15 min), and immediately followed by upregulation of Id2 (30 min). Between 8 and 16 h, both c-Myc and Id2 were down-regulated (FIG. 6A). Repression of c-Myc is a classical gene response to the antimitogenic cytokine TGF-β (28, 29). Accordingly, TGF-β also repressed Id2 in a variety of cell types (wild-type and p15$^{-/-}$ MEFs, Mv1Lu mink lung epithelial cells, and HaCaT human keratinocytes) (FIGS. 6B and 6C; and data not shown). Interestingly, c-Myc and Id2 were the only cell-cycle-related genes modified by TGF-β in wild-type and p15$^{-/-}$ MEFs (FIG. 6b; and data not shown for G1 cyclins, CDKs, and CDK inhibitors).

Downregulation of Id2 by TGF-β was essentially abolished in Mv1Lu expressing a tetracycline-regulated c-Myc gene, indicating that loss of c-Myc is indispensable for efficient repression of Id2 (FIG. 6C). Furthermore, using a c-Myc-ER fusion in Rat-1 cells (FIG. 6D), MEF cells, and NIH-3T3 cells, c-Myc activation by 4-OHT resulted in efficient induction of Id2 expression. Likewise, expression of wild-type c-Myc in MEFs elevated Id2 (FIG. 6E).

E. Activation of the Id2 Promoter by Myc Oncoproteins

Figure 7:
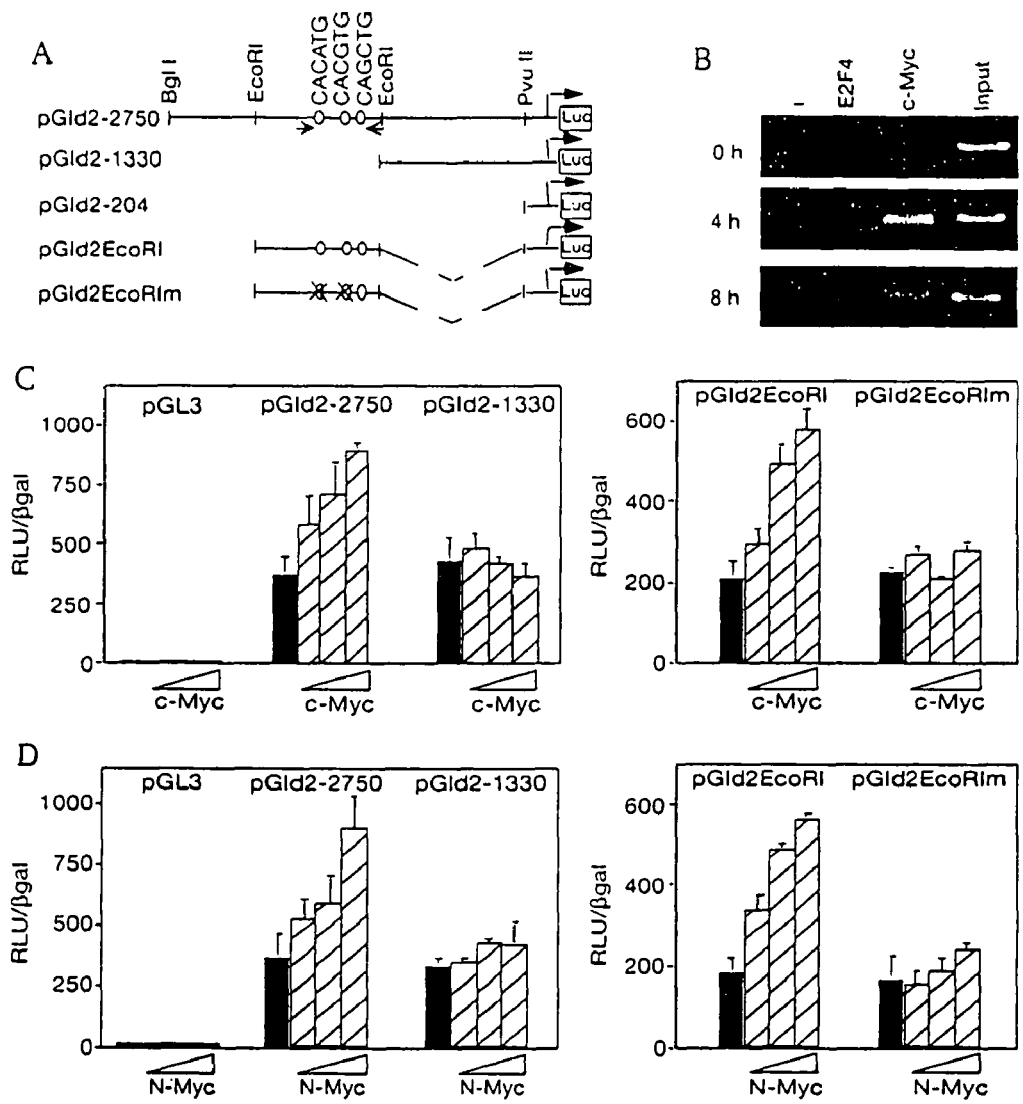
FIGS. 7A illustrate binding and transactivation of the Id2 promoter by Myc transcription factors.
FIG. 7B: Crosslinked chromatin was prepared from serum-starved TIG-3 (0 h) and from cells re-stimulated by serum for 4 h and 8 h. Chromatin was incubated without antibody (−), with anti-E2F4 antibody (E2F4), or with anti-c-Myc antibody (c-Myc). Immunoprecipitates were analyzed by PCR. Input is 0.02% of total input chromatin.
FIGS. 7C and 7D: 293 T cells were transfected with Id2-luciferase constructs in the absence (black bars) or presence (hatched bars) of increasing amounts of pcDNA3-c-Myc (7C) and pcDNA3-N-Myc (7D). Luciferase activity is quantified by the relative luminescence units (RLU) normalized to β-galactosidase activity.

To ascertain whether Myc oncoproteins upregulate Id2 at the transcriptional level, the inventors cloned the human Id2 promoter. The 5' region of human Id2 contains a cluster of three E-boxes that is fully conserved in mouse Id2 (FIG. 7A) (30). The three E-boxes are scattered throughout a region of 400 base pairs (bp) having 80% of its nucleotides identical to the mouse gene (data not shown). Two of the three E-boxes are high-affinity Myc-binding sites (CACATG at position −1,880 and CACGTG at position −1,590) (FIG. 7A). To determine whether the E-box cluster in the Id2 promoter binds c-Myc in vivo during the proliferation response of human fibroblasts to serum, the inventors used chromatin crosslinking (31). c-Myc did not initially bind to the Id2 promoter in quiescent fibroblasts, but it did after stimulation by serum (FIG. 7B). Furthermore, c-Myc and N-Myc transactivated a 2,900-bp Id2 promoter fragment in a dose-dependent manner (FIGS. 7C and 7D). Induction of the Id2 reporter by Myc transcription factors required the E-box cluster, as shown by loss of Myc responsiveness of Id2 promoter constructs lacking this cluster (FIGS. 7C and 7D for pGId2-1330; and data not shown for additional 5' deletion constructs).

To test whether the E-boxes in the Id2 promoter could mediate transcriptional activation by Myc oncoproteins, an EcoRI fragment containing wild-type or mutant Myc-binding sites was placed in front of a minimal Id2 promoter (pGId2-EcoRI and pGId2-EcoRIm, FIG. 7A). The reporter plasmid pGId2-EcoRI underwent dose-dependent activation by c-Myc and N-Myc, but mutations of the Myc-binding sites in pGId2-EcoRIm completely abolished this activation (FIGS. 7C and 7D).

F. Myc Requires Id2 to Bypass Rb

Figure 8:
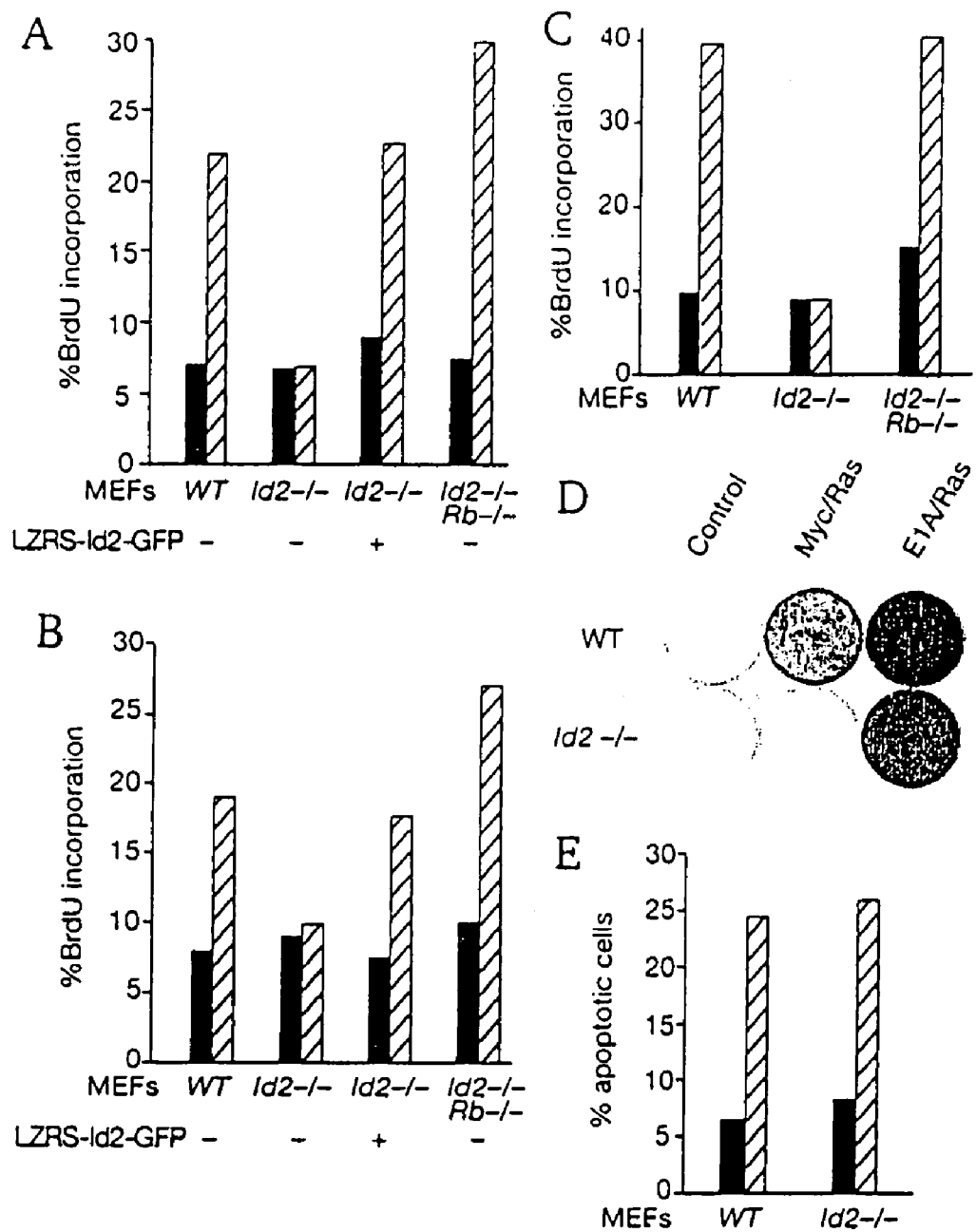
FIGS. 8A-8E portray a functional analysis of the Id2-Rb pathway in Myc-induced proliferation, transformation, and apoptosis.

Wild-type and Id2-null MEFs were infected with c-Myc-ER and N-Myc-ER retroviruses, and starved of serum. Activation of c-Myc-ER and N-Myc-ER by 4-OHT treatment induced entry into S phase of wild-type MEFs. This effect was absent in Id2-null MEFs, but was restored when Id2 was re-expressed before infection with Myc-ER retroviruses (FIGS. 8A and 8B). Expression of wild-type Myc prevented cell-cycle exit upon serum withdrawal in Id2$^{+/+}$ MEFs, but was ineffective in Id2-null MEFs (FIG. 8C). Similarly, ability of Myc to promote colony formation at low cell density was abolished in the absence of Id2 (data not shown). Interestingly, cell-cycle progression by Myc-ER activation and wild-type Myc expression was restored in MEFs from Id2$^{-/-}$ Rb$^{-/-}$ embryos, indicating that Myc requires Id2 to bypass Rb (FIGS. 8A, 8B, and 8C). Another Myc function, the cooperation with Ras for cellular transformation, was neutralized by loss of Id2; yet, Id2$^{-/-}$ MEFs could still be transformed by the combination of E1A and ras oncogenes (FIG. 8D). However, Myc-induced apoptosis was not compromised in Id2-null MEFs (FIG. 8E).

4. Discussion

The inventors show herein that Id2 function is essential for lethality and for the neurogenic and hematopoietic abnormalities caused by loss of Rb in the developing embryo. This is the first time that a protein partner of Rb, distinct from E2F transcription factors, has been shown to be essential for Rb function in vivo. Although the results disclosed herein clearly identify Id2 as a key target of Rb in normal cells, they also indicate that this scheme is subverted in neural cancer. There, the large amounts of Id2 that are generated as a direct consequence of genetic amplification of the N-myc oncogene neutralize the otherwise intact Rb pathway in these cells. Thus, Id2, a protein required to maintain the timing of differentiation in mammalian development, is transformed into the effector of a powerful oncogene in human cancer.

The hallmarks of the Rb mutant phenotype—ectopic cellular proliferation, loss of differentiation, and cell death—correspond to the consequences of uncontrolled Id2 activity (3, 4, 15, 32, 33). The analysis of Rb-Id2 double-mutant mice in the present example highlights Id2 as a downstream target of Rb during neurogenesis and erythropoiesis. Furthermore, the identification in normal cells of cell-cycle-regulated associations between Id2 and pocket proteins indicates that suppression of Id2 function by Rb is likely to be a general mechanism by which pocket proteins control progression of the cell cycle. The observations that Id2 (but not other Id proteins) is expressed in differentiating neuronal and hematopoietic cells (11, 34), and that these cell types are able to re-enter inappropriate proliferation and ultimately apoptosis in the absence of Rb, are consistent with the idea that maintenance of the postmitotic state requires physiological control of Id2 by Rb. Therefore, Id2 must target other factors during development and normal cell-cycle progression, and these targets must be activated following Rb-mediated inactivation of Id2.

Thus far, rescue of neurogenic and erythropoietic defects causing embryonic lethality of Rb mutant embryos has been accomplished by introduction of an Rblox minigene (8), by mutation of Id2 (as disclosed herein), and, partially, by mutation of E2F-1 (35). Clearly, in all three settings, Rb is indispensable in muscle differentiation and survival. This indicates that the role of Rb in muscle differentiation may be profoundly different from its function in neurogenesis and erythropoiesis. In addition, evidence that Id2 is expressed neither in differentiating skeletal muscle during embryogenesis, nor in myotubes from adult mice (36), indicates that physiological Rb targets in muscle cells have to be identified.

The large increase in Id2 in neuroblastoma cell lines (and primary tumors; data not shown) provides tumor cells with an epigenetic mechanism to bypass the tumor-suppressor function of Rb, in the absence of genetic alterations of the Rb pathway. The inventors speculate that other unknown mechanisms aimed at overriding the Rb pathway might operate in neuroblastoma cell lines without N-myc amplification/Id2 overexpression.

The results disclosed herein provide compelling evidence in favor of Id2 as a physiologically-relevant, direct target of Myc transcription factors. Two phenotypic hallmarks of Myc activation—the ability to promote cell-cycle entry in the absence of growth factors and the ability to cooperate with Ras to transform normal fibroblasts—are strictly dependent on the presence of Id2. Consequently, human neuroblastoma tumorigenesis, when sustained by N-myc gene amplification, is invariably associated with overexpression of Id2. The experiments in which Myc-expressing retroviruses are introduced in genetically-modified MEFs formally demonstrate a trivalent connection between Myc, Id2, and Rb, wherein Myc must induce Id2 to overcome an Rb-imposed cell-cycle block. However, in the absence of Rb, Id2 also becomes dispensable. This indicates that other Myc targets are sufficient to promote cell-cycle progression, if the entire Id2-Rb pathway is removed. The existence of additional Myc targets, possibly operating in a redundant manner with Id2, is also suggested by the apparent lack of major defects in Id2-null mice during embryogenesis (37) and by the intact ability of Myc to induce apoptosis in Id2-null MEFs (FIG. 8E).

EXAMPLE 2

Figure 9:
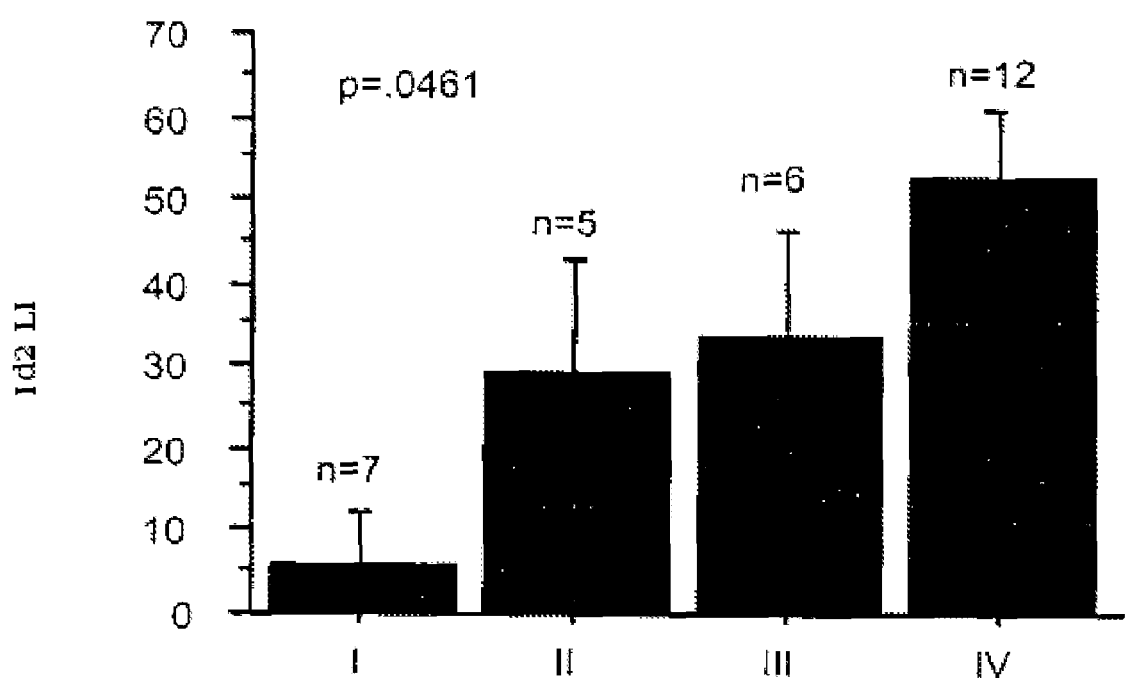
FIG. 9 depicts the expression of Id2, as determined by immunohistochemical staining in primary human neuroblastomas from patients with different tumor stages. Id2 labeling index (LI) is the percentage of Id2-positive cells in each tumor after counting >1,000 cells per sample. Note the significant correlation between Id2 LI and each clinical stage in neuroblastoma.

To validate the role of Id2 in promoting tumor growth of human neuroblastoma cells, the inventors analyzed the level of Id2 present in 32 primary neuroblastomas taken from patients with different clinical stages of the disease (favorable: Stages I and II; unfavorable: Stages III and IV). The inventors found a highly significant association between expression of Id2 and unfavorable clinical stage (p=0.0091) (Table 2). Furthermore, the Id2 labeling index (LI) (% of tumor cells expressing Id2 in each tumor) is significantly higher in the most advanced, unfavorable stages of neuroblastoma (FIG. 9).

TABLE 2

Correlation between Id2 expression and Clinical Stage in Neuroblastomas

| Stage | Id2 Positive No. | % | Id2 Negative No. | % | Odds Ratio | 95% CI | p |
|---|---|---|---|---|---|---|---|
| Favorable | 5 | 26 | 8 | 67 | 5.6 | 1.2-27.0 | 0.0091 |
| Unfavorable | 14 | 74 | 4 | 33 | | | |

Figure 10:
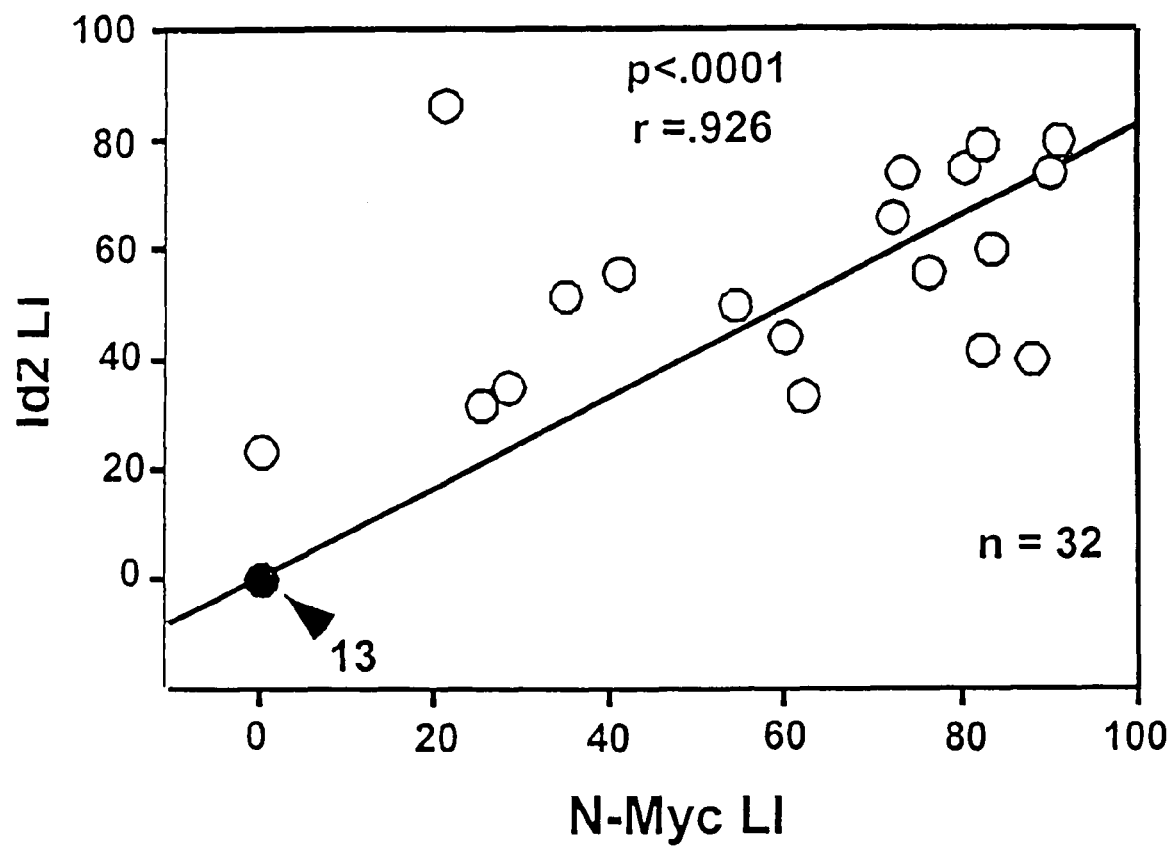
FIG. 10 shows the expression of N-Myc and Id2, as determined by immunohistochemical staining in 32 primary human neuroblastomas. Id2 and N-Myc labeling indexes (LIs) are the percentage of N-Myc- and Id2-positive cells in each tumor after counting >1,000 cells per sample. Note the highly significant correlation between N-Myc LI and Id2 LI in neuroblastoma.

The inventors also compared the levels of Id2 and the levels of N-myc present in neuroblastomas. The inventors found an essentially perfect correlation between Id2 LI and N-Myc LI in primary neuroblastomas (FIG. 10). These data strongly support and extend the theory that Id2 mediates N-myc tumorigenic effect in human neuroblastomas.

Figure 11:
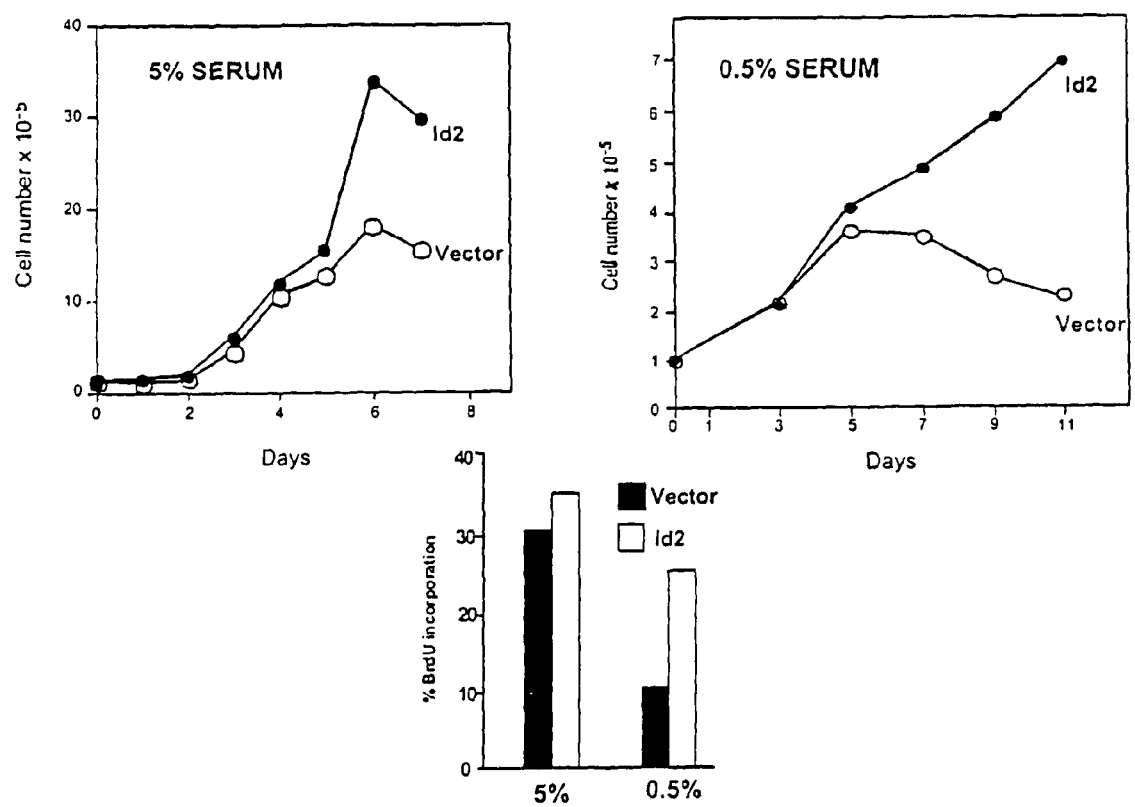
FIG. 11 illustrates that Id2 amounts comparable to those expressed by human neuroblastoma cells were introduced in NIH-3T3 fibroblasts by retroviral infection. Cells infected with a control vector (vector) or with an Id2 expression vector (Id2) were grown in 5% serum to measure saturation density (top left), or in low (0.5%) serum (top right). The S-phase fraction of vector- and Id2-infected cells was determined by BrdU incorporation (bottom panel). Note that NIH-3T3 fibroblasts expressing Id2 reach higher saturation densities in normal serum, and are able to grow and incorporate BrdU in low serum.

To test whether the amounts of Id2 expressed by neuroblastoma cells are sufficient to render non-tumorigenic cells similar to tumor cells, the inventors used an Id2-expressing retrovirus to introduce Id2 into normal fibroblasts (NIH-3T3) at levels comparable to those present in neuroblastomas. Simply introducing Id2 into these cells resulted in their ability to grow in the absence of serum, and to reach very high saturation densities (FIG. 11). These features are hallmarks of cancer cells. Therefore, these results demonstrate that normal cells gain the hallmarks of cancer cells when forced to express Id2 at levels similar to those present in human neuroblastomas.

Figure 12:
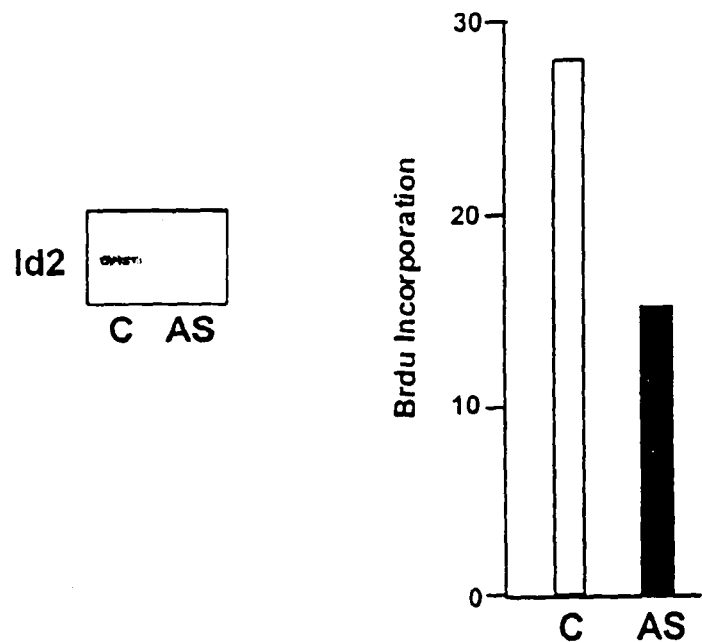
FIG. 12 depicts Id2 antisense oligonucleotides (AS) or control mismatched oligonucleotides (C) that were introduced in the human neuroblastoma cell line LAN-1 by lipofection. A Western blot against Id2 shows significant reduction of Id2 protein in cells transfected with anti-Id2 oligonucleotides, as compared to cells transfected with control mismatched oligonucleotides (left panel). Reduction of Id2 is associated with a decreased S-phase, as measured by BrdU incorporation (right panel).

The results from this example have further reinforced the inventors' determination to search for small-molecule inhibitors of Id2 that might be used therapeutically to treat neuroblastomas and other cancers. To this end, the inventors used a lipophilic vehicle to introduce Id2 antisense oligonucleotides into human neuroblastoma cells (LAN-1) that express high amounts of Id2. By this method, the inventors successfully reduced the levels of Id2 in LAN-1 cells by at least 80% (FIG. 12). The enforced decrease of Id2 resulted in a significant reduction in the ability of these cells to grow, as measured by the reduction of incorporation of BrdU into their DNA (FIG. 12). It is believed that this is the first time that antisense molecules against Id2 have been used successfully in human neuroblastomas.

EXAMPLE 3

1. Introduction

Id proteins are "integrators" of positive and negative environmental stimuli, in that they integrate these stimuli into the transcriptional machinery that regulates differentiation (1, 51). One member of the Id family, Id2, coordinates inhibition of differentiation and stimulation of cell proliferation by inactivating the Rb tumor suppressor protein (3, 4). Id2 operates, at least in part, under control of Myc proto-oncogenes, which directly bind to, and activate, the Id2 promoter (52). By raising Id2 levels, Myc proteins circumvent the block on cell-cycle progression that is imposed by the Rb pathway. Not surprisingly, tumor cells with oncogenic activation of Myc, such as the neuroblastoma cell lines carrying N-myc gene amplification, overexpress Id2 to constitutively bypass the cell-cycle checkpoint imposed by Rb (52).

Previous studies have proposed that the different biologic properties of Rb and Rb family members result from their ability to regulate E2F transcription factors (53-55). The inventors' recent results from genetic intercrosses of Rb and Id2 knockout mice indicated that negative control of Id2 activity is an additional requirement for Rb function in vivo (52). In the present study, the inventors analyzed the expression of N-Myc and Id2 during normal development and in primary neuroblastoma. Because of the crucial importance ascribed to loss of Rb function in human cancer, the inventors investigated whether overexpression of Id2 induced cellular transformation and predicted clinical outcome in children with neuroblastoma. Having found that Id2 expression is a prognostic determinant in neuroblastoma, the inventors asked whether inhibition of Id2 could serve as a point of intervention in cancer by studying the consequences of eliminating Id2 from primary and tumor cells.

2. Materials and Methods

A. Patient Population and Statistical Methods

The inventors analyzed 47 primary neuroblastoma samples from 47 patients diagnosed and treated between 1991 and 2000 at the Ospedale Pediatrico Bambino Gesu (Rome, Italy). Median follow-up was 46 months (range: 12-108 months). Staging was performed according to the International Neuroblastoma Staging System criteria. Patient population included 8 Stage 1, 8 Stage 2, 9 Stage 3, 21 Stage 4, and 1 Stage 4S. Stages 1, 2, and 4S were classified as favorable, whereas Stages 3 and 4 were unfavorable. Event-free survival time for each patient was defined as the time from the date of diagnosis to the date of earliest occurrence of recurrence, disease progression, or death resulting from any cause.

The Pearson correlation coefficient was used to test the strength of association between the continuous variables. Associations among Id2 expression and other prognostic variables were examined by the Chi-square test. Survival analyses were performed according to the method of Kaplan and Meier, and comparisons of outcome between subgroups were performed by the log rank test for univariate comparisons. For multivariate analysis, Cox's proportional hazard regression model was applied. Statistical analyses were performed using StatView 4.1 (Abacus Concepts, Inc., Berkeley, Calif.).

B. Immunohistochemistry

Figure 14:
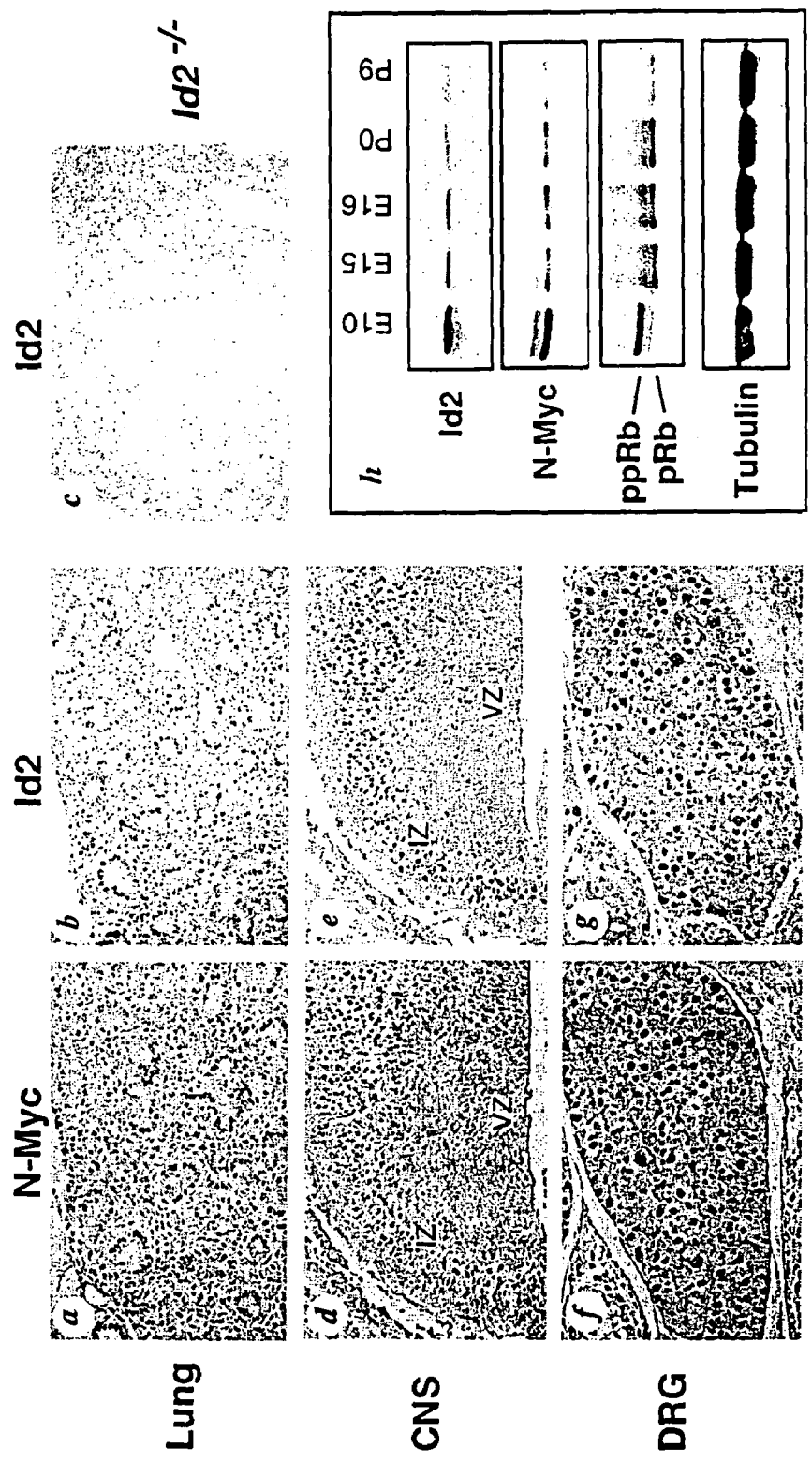
FIG. 14 sets forth an immunohistochemical analysis of N-Myc and Id2 in 15-day mouse embryo. N-Myc and Id2 show an overlapping pattern of nuclear staining in the alveolar epithelium of the lung (panels a and b), the intermediate zone of the telencephalon (panels d and e), and dorsal root ganglia (panels f and g). Specificity of Id2 staining is demonstrated by the absence of immunoperoxidase activity in the lung of Id2$^{-/-}$ embryo (panel c). Original magnification was ×25 magnification (panels a-g). Panel h presents a Western immunoblot analysis of N-Myc, Id2, Rb, and α-tubulin in the mouse brain during development. ppRb/pRb ratios from a quantitative densitometric analysis of the Rb blot are: E10: 7.0; E15: 0.31; E16: 0.26; P0: 0.10; P9: 0.04. pRb: hypophosphorylated Rb; ppRb: hyperphosphorylated Rb

Antibodies used for immunohistochemistry included a previously characterized anti-N-Myc monoclonal antibody, at a concentration of 10 µg/ml (56) (Oncogene Research Products, Boston, Mass.), and the anti-Id2 polyclonal antibody, C-20, at a concentration of 2 µg/ml (Santa Cruz Biotechnology, Santa Cruz, Calif.). Specificity of Id2 immunostaining was assessed by preabsorption of the antibody with the peptide from which the antibody was raised. This, but not preabsorption with a non-relevant peptide, abolished Id2 staining. Controls using polyclonal rabbit immunoglobulin, instead of primary antibody, showed no evidence of staining. Additionally, tissues from Id2-null mice provided a negative control for Id2 antibody (FIG. 14, panel c). Immunohistochemical results of N-Myc and Id2 staining in neuroblastoma were scored independently by the inventors. At least 600 cells from 5-10 high-power fields were scored for each tumor sample.

C. Immunoblot Analysis

Mouse embryo tissues were collected on dry ice, and proteins were extracted with RIPA buffer in the presence of protease and phosphatase inhibitors. The antibodies used for immunoblotting were anti-Id2 (C-20; Santa Cruz Biotechnology, Santa Cruz, Calif.), anti-N-Myc (Oncogene Research Products, Boston, Mass.), and anti-Rb (G3-245; Pharmingen, San Diego, Calif.).

D. Growth Experiments and Antisense Oligonucleotide Transfections

Primary MEFs were obtained from 13.5-day-old embryos, and cultured as described (52). Passage 4 cells were plated at a density of $3 \times 10^4$ per 35-mm dish, and counted on the indicated days. Unless otherwise specified, cells were cultured in DMEM supplemented with 10% fetal bovine serum (Sigma). Retroviral infection of NIH-3T3 cells was done as described (52). For saturation density experiments, cells were plated in DMEM containing 5% fetal bovine serum, and cultivated for up to 7 days. Cells were counted daily with a hemocytometer. For growth in soft agar of NIH-3T3 derivatives and LAN1, $5 \times 10^4$ and $1 \times 10^5$ cells, respectively, were plated in 35-mm dishes in 0.33% agar solution (BiTek, DIFCO) in DMEM containing 5% fetal bovine serum. The bottom layer was prepared using 0.6% agar in growth medium. After 7 days, 1.5 ml of agar mixture were added. Colonies were scored in triplicate wells after incubation for 14 days.

Phosphorothioate oligonucleotides complementary to human Id2 and the mismatched control were obtained from Gibco BRL. The sequences of the oligonucleotides were as follows: Id2-AS, 5'-AGGCTTTCATGCTGACCGC-3' (SEQ ID NO: 5); Id2-MSM, 5'-GCGAGTTGTCGCACGGTCT-3' (SEQ ID NO: 6). Oligonucleotides were mixed with Superfect (Qiagen) according to the manufacturer's instructions, and were used to treat LAN1 cells at the final concentration of 0.8 M. After incubation for 24 h, cells were analyzed for the ability to incorporate BrdU and form colonies in soft agar.

3. Results

A. N-Myc and Id2 Display an Overlapping Pattern of Expression During Development The inventors performed an immunohistochemical analysis of N-Myc and Id2 proteins in the mouse embryo at mid-gestation (embryonic day 15, E15). At this stage of development, Rb is essential for cell-cycle withdrawal and differentiation of neural progenitors (9, 27). The inventors found a striking overlap between the pattern of expression of N-Myc and Id2 in epithelial and neural tissues (FIG. 14).

Lung is an example of abundant expression of N-Myc and Id2 proteins in the epithelium without any detectable signal in the adjacent mesenchyme (FIG. 14, panels a-c). A similar pattern of expression is present in the small intestine (data not shown). During early neurogenesis (before day E12), N-Myc and Id2 are expressed in the telencephalon throughout the proliferating ventricular zone (10, 11, 57). However, at E15, the two proteins appear in the intermediate zone, which predominantly contains post-mitotic neurons (FIG. 14, panels d and e). Positive staining in the ventricular and sub-ventricular layers is detectable only in small areas of the olfactory lobe and the hippocampus (data not shown). N-Myc and Id2 are also abundant in large, differentiated neurons of dorsal root and trigeminal ganglia, which fail to incorporate BrdU at this stage of development (FIG. 14, panels f and g; and data not shown).

To determine the time at which active Rb appears in the brain, and the manner in which it relates to N-Myc and Id2, the inventors compared expression of N-Myc, Id2, and Rb in embryonic and post-natal brains, using Western immunoblot analysis (FIG. 14, panel h). Although expression of N-Myc and Id2 decreased with development, significant amounts of the two proteins were found at E15, and were still detectable after 9 days of post-natal life. Rb undergoes a change from hyperphosphorylated form (abundant at E10) to hypophosphorylated, active form by E15. Thus, expression of N-Myc and Id2 is detectable at mid-gestation in predominantly post-mitotic neuroectodermal tissues, and is paralleled by a shift of Rb from inactive to active form.

B. Id2 Expression is Predictive of Poor Survival of Neuroblastoma Patients

Figure 15:
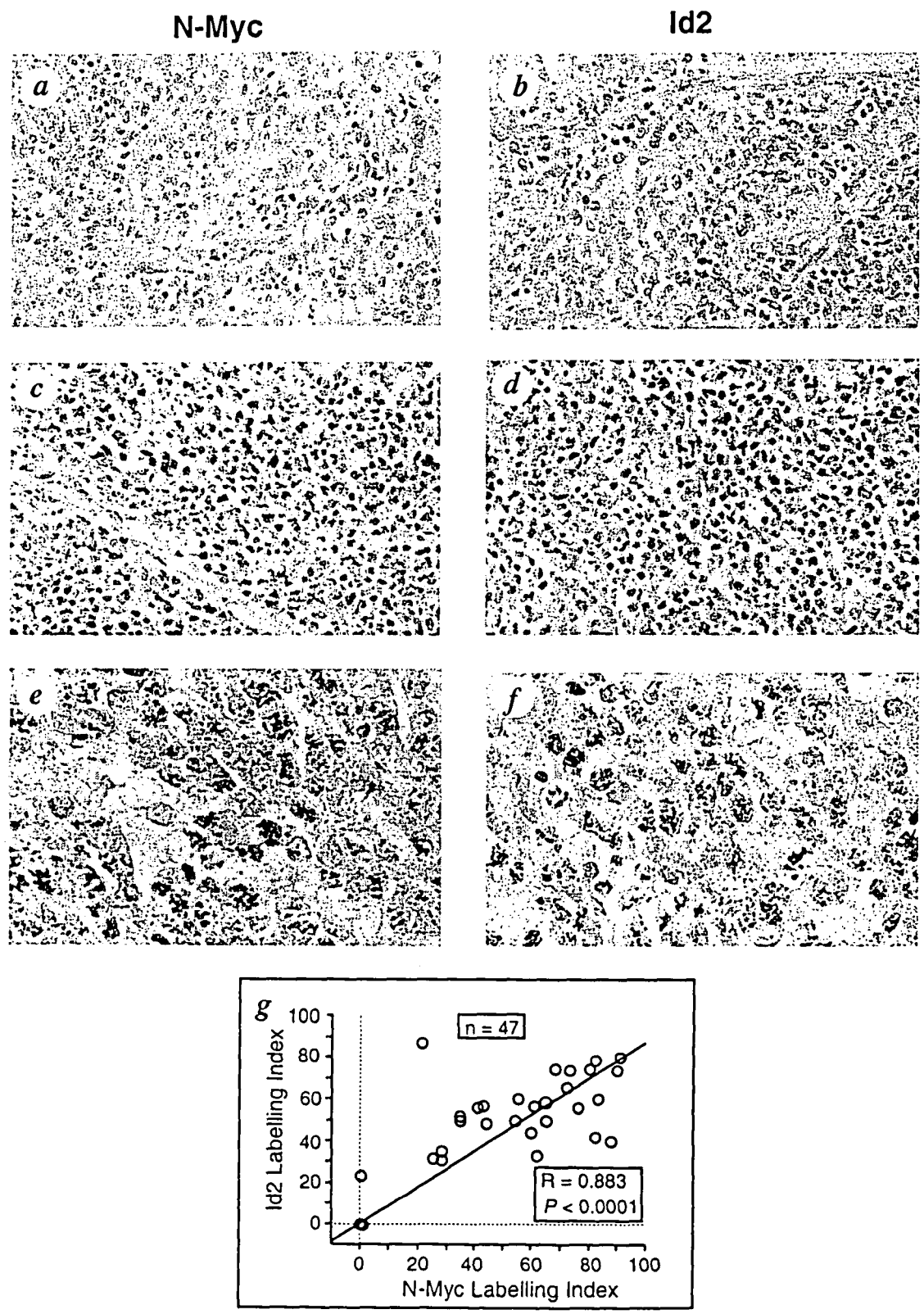
FIG. 15 shows an analysis of N-Myc and Id2 proteins in neuroblastoma. Immunohistochemistry of serial tumor sections shows the absence of N-Myc (panel a) and Id2 (panel b) in a stage 1 neuroblastoma patient (×25). The majority of cells in a stage 4 neuroblastoma (×25) expressed high levels of N-Myc (panel c) and Id2 (panel d) proteins. Higher magnification (×100) demonstrates prevalent nuclear localization of N-Myc (panel e) and Id2 (panel f). Panel g shows a scatter plot of N-Myc labeling index (LI) versus Id2 LI for neuroblastoma. LI is defined as the percentage of neuroblastoma cells that stained positive after counting at least 600 cells for each tumor. Eighteen (18) samples lacking N-Myc and Id2 immunostaining are portrayed as a thick symbol at the origin of the two axes. The line of best fit is shown with a Pearson correlation coefficient of 0.868.

To determine whether the "N-Myc-Id2 pathway" is activated in neuroblastoma cells before tissue culture, and whether Id2 expression correlates with clinical behavior, the inventors conducted an immunohistochemical analysis for the proteins N-Myc and Id2 in 47 primary neuroblastomas. N-Myc and Id2 were not expressed in post-natal adrenal medulla, the most common site of origin of neuroblastoma in humans (data not shown). N-Myc and Id2 were either absent ("negative" samples; FIG. 15, panels a and b) or detectable in the nuclei of 25% or more tumor cells ("positive" samples; FIG. 15, panels c-f).

In the inventors' series, there were 8 tumors with N-myc gene amplification (Table 3). All showed positive staining for N-Myc and Id2. Among the 37 tumors without N-myc gene amplification, 19 had N-Myc protein expression. These findings confirm results from previous studies, which indicated that mechanisms other than gene amplification lead to deregulated expression of N-Myc in a significant number of neuroblastomas (56, 58, 59). With the exception of one case (N-Myc negative/Id2 positive), the inventors found an invariable correlation between the expression of N-Myc and Id2 (28 tumors were N-Myc positive/Id2 positive; 18 tumors were N-Myc negative/Id2 negative).

Figure 16:
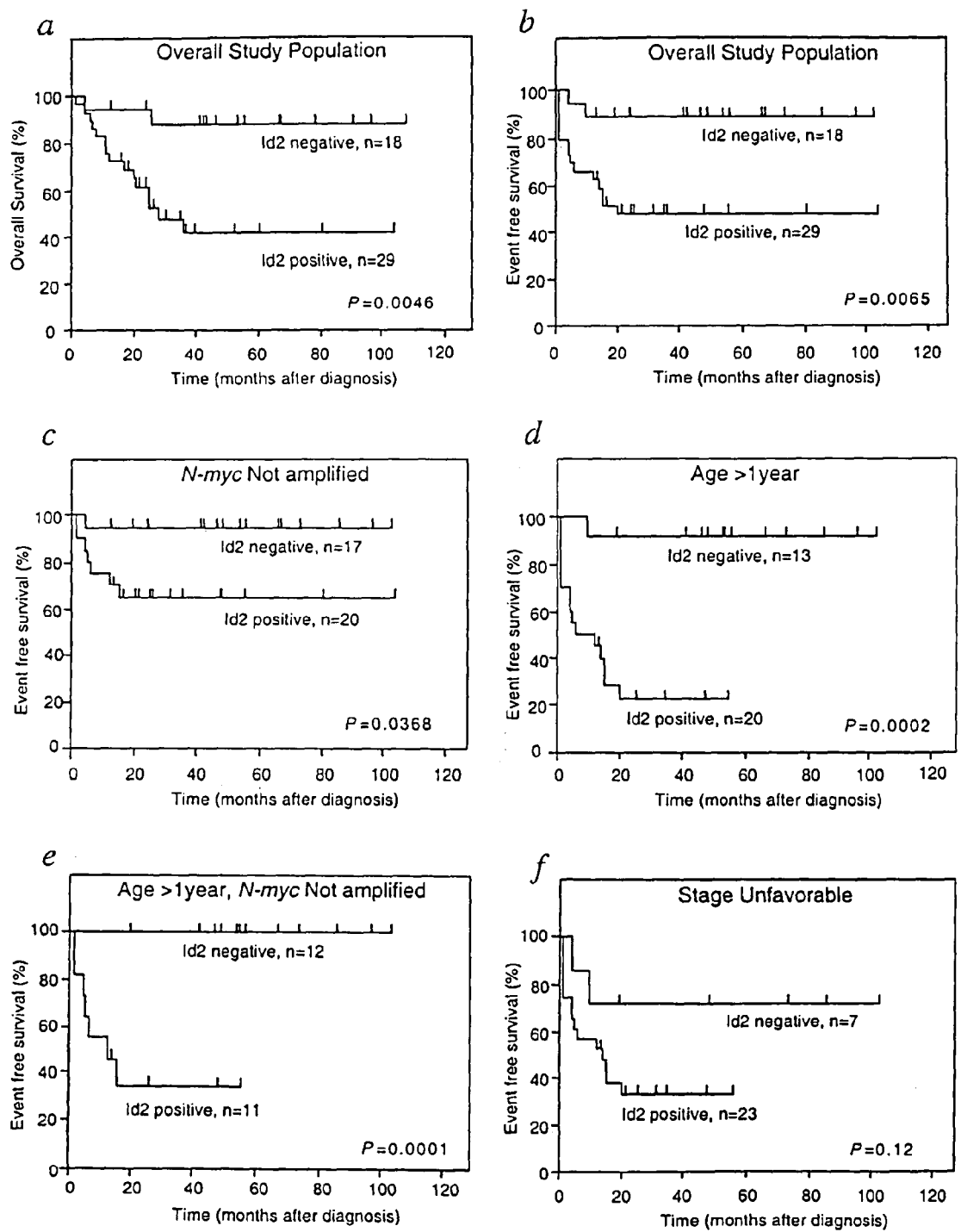
FIG. 16 presents Kaplan-Meier curves of neuroblastoma patients according to Id2 status. Id2 expression is associated with decreased overall (panel a) and event-free survival (panel b) in the entire series of patients tested. Event-free survival for patients without N-myc amplification (panel c), age >1 year (panel d), age >1 year without N-myc amplification (panel e), and unfavorable stages (panel f) are shown.

The inventors scored the percentage of neuroblastoma cells in each tumor that stained positive for N-Myc and Id2 (labeling index, LI), and found that the LIs for N-Myc and Id2 were highly correlated (Pearson Correlation co-efficient=0.868, P<0.0001; FIG. 15, panel g). Next, the inventors examined the correlation between Id2 expression and clinical behavior of neuroblastoma. On all patients, the cumulative overall and event-free survivals of Id2-negative tumors were 0.877±0.082 and 0.889±0.074 versus 0.417±0.103 and 0.472±0.094 for Id2-positive tumors (FIG. 16, panels a and b). The Kaplan-Meier analysis showed that Id2 expression was predictive of increased mortality (FIG. 16, panels a and b; Log-rank P-values=0.0046 and 0.0065 for overall and event-free survival, respectively).

TABLE 3

Patient demographics and statistical analysis comparing Id2 status to clinical features

| | | Total n (%) | Id2 positive n (%) | Id2 negative n (%) | P-value[A] |
|---|---|---|---|---|---|
| Age | <1 year | 14 (29.8) | 9 (19) | 5 (10) | 0.8 |
| | >1 year | 33 (70.2) | 20 (43) | 13 (28) | |
| Stage | Favorable | 17 (36.2) | 6 (13) | 11 (23) | 0.0051 |
| | Unfavorable | 30 (63.8) | 23 (62) | 7 (15) | |
| N-myc gene | <3 copies | 37 (78.7) | 20 (43) | 17 (36) | 0.015 |
| | >3 copies | 8 (17.8) | 8 (17) | 0 (0) | |
| | Unknown | 2 (4.2) | 1 (2) | 1 (2) | |
| Events | No event | 30 (63.8) | 14 (30) | 16 (34) | 0.0048 |
| | Event | 17 (36.2) | 15 (32) | 2 (2) | |

Id2-positive samples contained ≧25% tumor cells that stained for Id2. Id2-negative samples did not contain tumor cells with Id2 staining. No tumor showed Id2 positivity >0% and <25%. [A]Chi-square P-value The outcome of neuroblastoma patients aged less than 1 year is good, regardless of other prognostic variables (60). Conversely, patients with N-myc gene amplification display an invariably poor prognosis (61). Therefore, the inventors asked whether Id2 remains a predictive indicator for patients older than 1 year of age and/or lacking N-myc gene amplification. Kaplan-Meier plots of event-free survival showed that Id2 expression was associated with increased mortality in each subgroup (FIG. 16, panels c-e). Chi-square analysis demonstrated a positive correlation between Id2 expression and unfavorable clinical stages (Table 3; P=0.0051). When outcome was evaluated in this subgroup of patients, there was a trend towards a correlation between Id2 expression and low event-free survival (P=0.12; FIG. 16, panel f). In a multivariate Cox proportional hazard model that included Id2 expression (positive), age (<1 year), and N-myc copy number (>3 copies), Id2 expression was the strongest independent predictor of disease-free survival (P=0.0264, relative hazard 10.996, Table 4).

TABLE 4

Multivariate Cox regression analysis[A]

| Covariate | Relative Hazard | Confidence Interval | P-value |
|---|---|---|---|
| Id2 expression (positive) | 10.996 | 1.325-9.1286 | 0.0264 |
| Age (<1 year) | 0.122 | 0.015-1.010 | 0.0511 |
| N-myc amplification (>3 copies) | 1.733 | 0.583-5.155 | 0.3288 |

[A]n = 47

Figure 17:
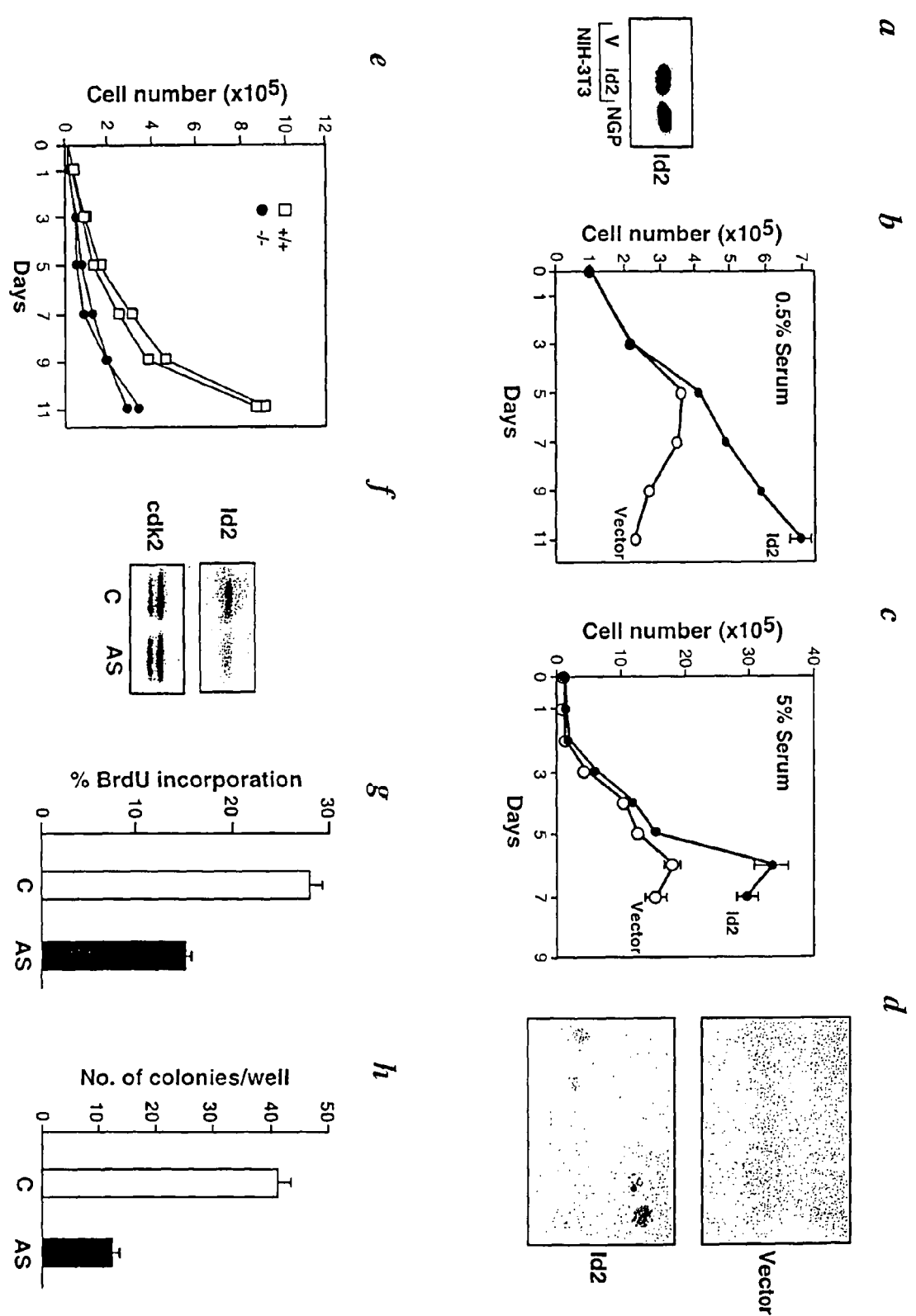
FIG. 17 illustrates that Id2 transforms NIH-3T3 cells, and is required for cell proliferation in normal and tumor cells. As panel a shows, lysates from NIH-3T3 cells infected with LZRS-GFP (V) and LZRS-Id2-GFP (Id2), and from the neuroblastoma cell line, NGP (NGP), were analyzed by Western immunoblot for expression of Id2. Panels b and c illustrate proliferation in 0.5% FBS (panel b) and 5% FBS (panel c) of NIH-3T3-vector (white circles) and NIH-3T3-Id2 (black circles). The cell number at each time point represents the average and standard deviation of duplicate samples. Panel d illustrates anchorage-independent growth of NIH-3T3-vector and NIH-3T3-Id2. Cells were assayed for their ability to grow in soft agar, and photographed after 14 days in culture. As panel e shows, passage 4 primary MEFs from two independent litters containing wild-type (white squares) and Id2$^{-/-}$ littermates (black circles) were plated in triplicate in 10%

C. Id2 Transforms NIH-3T3 Cells, and is a Rate-Limiting Factor for Proliferation of Fibroblasts and Neuroblastoma To determine whether the large amounts of Id2 expressed by neuroblastoma cells are sufficient to induce transformation, the inventors introduced Id2 into NIH-3T3 cells. NIH-3T3 cells transduced with LZRS-GFP-Id2 retrovirus (NIH-3T3-Id2) expressed levels of Id2 protein comparable to the endogenous levels of Id2 in neuroblastoma cells carrying amplification and overexpression of the N-myc oncogene (FIG. 17, panel a). NIH-3T3-Id2 cells overcame the serum requirement of vector-infected NIH-3T3 cells for entry into S-phase and long-term proliferation (FIG. 17, panel b; and data not shown). In the presence of high levels of Id2, cells overgrew a monolayer doubling the saturation density of control cells (FIG. 17, panel c). As a further sign of transformation, NIH-3T3-Id2 cells, when cultured in soft agar, formed distinct foci (29±5 colonies per well); such foci were absent in cultures of vector-infected NIH-3T3 cells (FIG. 17, panel d). However, NIH-3T3-Id2 cells were not tumorigenic when injected into nude mice (data not shown).

To assess the consequences of loss of Id2 function on cell proliferation, the inventors analyzed mouse embryo fibroblasts (MEFs) derived from $Id2^{+/+}$ and $Id2^{-/-}$ embryos. $Id2^{-/-}$ MEFs showed a noticeably lower rate of division (FIG. 17, panel e). The defective ability to grow persisted when the inventors compared 3T3 derivatives from $Id2^{-/-}$ MEFs with their wild-type counterparts, indicating that immortalization was not sufficient to overcome the requirement for Id2 (data not shown).

The inventors next sought to determine whether opposing the uncontrolled expression of Id2 in neuroblastoma cells could affect the cells' malignant behavior. For these experiments, the inventors used the neuroblastoma cell line, LAN1, that carries N-myc amplification and Id2 overexpression (52). Treatment of LAN1 with a phosphorothioate Id2 antisense oligonucleotide for 24 h led to a decrease of endogenous Id2 by approximately 60%, compared to a mismatch oligonucleotide (FIG. 17, panel f). Consistent with reduction of Id2, BrdU incorporation showed decreased S-phase entry (15% versus 28%, in mismatched treated cells; FIG. 17, panel g). Interestingly, reduction of Id2 protein levels in LAN1 led to an even stronger effect on the ability of these cells to form colonies in soft agar (from 41±3 colonies per well for mismatched-treated LAN1, to 12±2 colonies per well for anti-Id2-treated cells; FIG. 17, panel h). These results suggest that lowering Id2 in neuroblastoma may generate anti-tumor mechanisms involving more than antiproliferative effects.

4. Discussion

During development of the nervous system, Rb is not required for induction of neuronal determination and migration of neural progenitors from the ventricular zone to post-mitotic areas of the brain; however, Rb is essential for neurons to exit the cell cycle and survive (27). In the absence of Rb, neurons undergo ectopic proliferation and apoptosis (9). These defects are rescued by ablation of Id2 in vivo, and are recapitulated in vitro by overexpressing Id2 in normal cortical progenitors (52, 62).

Previous studies proposed that loss of Id proteins from the proliferating zones of the brain, which occurs during early neurogenesis, initiates neuronal gene expression and differentiation (10, 11, 63). The inventors suggest herein that permanent elimination of Ids from the ventricular zone renders these early events insensitive to the genetic inactivation of Rb. However, persistent expression of the "N-Myc-Id2 pathway" in post-mitotic areas of the CNS and PNS may dictate the window of Rb requirement. In this model, Rb is essential, during mid-gestation in post-mitotic areas of the nervous system, for controlling Id2 function, executing terminal cell-cycle withdrawal, completing differentiation, and securing survival of neuronal cells.

To the inventors' knowledge, Id2 is the first transcriptional target of N-Myc the expression of which correlates with the N-Myc protein during development and in neuroblastoma. The immunohistochemical analysis of Id2 in neuroblastoma shows that tumor aggressiveness depends, at least in part, on activation of the "N-Myc-Id2 pathway". In the inventors' series, of the 17 patients who relapsed and/or died, 15 (88%) overexpressed Id2 and 2 (12%) did not. Therefore, the vast majority of prognostically-unfavorable neuroblastoma deregulates Id2 expression.

Although N-myc gene amplification is a well-established adverse prognostic indicator in neuroblastoma, the significance of N-Myc protein expression is still debated (56, 58, 59, 64). In the inventors' series, expression of Id2 correlates with N-Myc (FIG. 15, panel g). However, the unique feature of an assay of Id2 in neuroblastoma is that its expression integrates the effects of N-myc activation, and possibly other upstream signals, to overcome the crucial tumor suppressor function of the Rb pathway.

A number of studies have suggested that inactivation of the Rb pathway is a determinant of poor prognosis for cancer patients (65-67). The inventors propose that neuroblastoma with favorable outcome may retain a functional Rb pathway, whereas Id2-independent mechanisms for Rb inactivation may be present in the small subgroup of unfavorable, Id2-negative neuroblastoma. The analysis of Id2 expression has considerable potential to be of practical use in the routine assessment of neuroblastoma patients. This is strengthened by the fact that immunohistochemical tests for Id2 expression are inexpensive, and could easily be available to most medical centers.

The inventors' studies on the role of Id2 in cellular proliferation show that loss of Id2 significantly reduces the rate of cellular proliferation of primary and immortalized embryonic fibroblasts. These data are consistent with previous reports showing an impaired proliferation rate of other cell types from $Id2^{-/-}$ mice (68, 69). It is likely that a critical threshold of Id2 determines the rate of proliferation in primary cells. Support for this hypothesis may be found in the inventors' results showing that overexpression of Id2, at levels comparable to those found in neuroblastoma cells, renders cells insensitive to such extracellular antimitogenic signals as serum deprivation and contact inhibition, thereby conferring oncogenic potential. The role of Id2 as an oncogenic factor in neuroblastoma is specifically supported by reduced entry into S phase, and severely compromised anchorage-independent growth of neuroblastoma cells, where Id2 expression has been forcibly reduced by antisense oligonucleotides.

In human tumors, Rb is functionally inactivated by genetic alterations of the "Rb pathway", or by constitutive activation of the "N-Myc-Id2 pathway". The inventors have now shown that Id2 expression determines the rate of proliferation of primary, immortalized, and tumor cell lines. These observations suggest that Id2 will make a major contribution to the inappropriate cell proliferation that results from loss of the negative control of Rb upon Id2 in tumors with genetic alterations of the "Rb pathway". Anti-Id2 therapeutic approaches might be attractive new tools, even in tumors where inactivation of Rb results from mechanisms other than the activation of the "Myc-Id2 pathway".

REFERENCES

1. Norton et al., Id helix-loop-helix proteins in cell growth and differentiation. *Trends Cell Biol.*, 8:58-65, 1998.
2. Massari and Murre, Helix-loop-helix proteins: regulators of transcription in eucaryotic organisms. *Mol. Cell. Biol.*, 20:429-440, 2000.
3. Iavarone et al., The helix-loop-helix protein Id-2 enhances cell proliferation and binds to the retinoblastoma protein. *Genes Dev.*, 8:1270-84, 1994.
4. Lasorella et al., Id2 specifically alters regulation of the cell cycle by tumor suppressor proteins. *Mol. Cell. Biol.*, 16:2570-78, 1996.
5. Clarke et al., Requirement for a functional Rb-1 gene in murine development. *Nature*, 359:328-30, 1992.
6. Jacks et al., Effects of an Rb mutation in the mouse. *Nature*, 359:295-300, 1992.
7. Lee et al., Mice deficient for Rb are nonviable and show defects in neurogenesis and hematopoiesis. *Nature*, 359:288-94, 1992.
8. Zacksenhaus et al., pRb controls proliferation, differentiation, and death of skeletal muscle cells and other lineages during embryogenesis. *Genes Dev.*, 10:3051-64, 1996.
9. Lee et al., Dual roles of the retinoblastoma protein in cell cycle regulation and neuron differentiation. *Genes Dev.*, 8:2008-21, 1994.
10. Jen et al., Each member of the Id gene family exhibits a unique expression pattern in mouse gastrulation and neurogenesis. *Dev. Dyn.*, 208:92-106, 1997.
11. Neuman et al., Neuronal expression of regulatory helix-loop-helix factor Id2 gene in mouse. *Dev. Biol.*, 160:186-195, 1993.
12. Zhu et al., Id gene expression during development and molecular cloning of the human Id-1 gene. *Brain Res. Mol. Brain Res.*, 30:312-326, 1995.
13. Sherr, C. J., Cancer cell cycles. *Science*, 274:1672-77, 1996.
14. Weinberg, R. A., The retinoblastoma protein and cell cycle control. *Cell*, 81:323-30, 1995.
15. Martinsen and Bronner-Fraser, Neural crest specification regulated by the helix-loop-helix repressor Id2. *Science*, 281:988-91, 1998.
16. Maris and Matthay, Molecular biology of neuroblastoma. *J. Clin. Oncol.*, 17:2264-79, 1999.
17. Easton et al., Disruption of the cyclin D/cyclin-dependent kinase/INK4/retinoblastoma protein regulatory pathway in human neuroblastoma. *Cancer Res.*, 58:2624-32, 1998.
18. Beltinger et al., No CDKN2 mutations in neuroblastomas. *Cancer Res.*, 55:2053-55, 1995.
19. Diccianni et al., The p16 and p18 tumor suppressor genes in neuroblastoma: implications for drug resistance. *Cancer Lett.*, 104:183-192, 1996.
20. Diccianni et al., Frequent deregulation of p16 and the p16/G1 cell cycle-regulatory pathway in neuroblastoma. *Int. J. Cancer*, 80:145-154, 1999.
21. Castresana et al., Mutational analysis of the p16 gene in human neuroblastomas. *Mol. Carcinog.*, 18:129-133, 1997.
22. Kawamata et al., Molecular analysis of the cyclin-dependent kinase inhibitor family: p16(CDKN2/MTS1/INK4A), p18(INK4C) and p27(Kipl) genes in neuroblastomas. *Cancer*, 77:570-575, 1996.
23. Fan et al., Lack of gene amplification as a mechanism of CDK4 activation in human neuroblastoma. *Oncol. Rep.*, 6:647-50, 1999.
24. Alevizopoulos et al., Cyclin E and c-Myc promote cell proliferation in the presence of p16INK4a and of hypophosphorylated retinoblastoma family proteins. *EMBO J.*, 16:5322-33, 1997.
25. Goodrich and Lee, Abrogation by c-Myc of G1 phase arrest induced by RB protein but not by p53 [published erratum: *Nature*, 360:491, 1992]. *Nature*, 360:177-179, 1992.
26. Amati et al., Myc and the cell cycle. *Front Biosci.*, 3:D250-268, 1998.
27. Slack et al., A critical temporal requirement for the retinoblastoma protein family during neuronal determination. *J. Cell Biol.*, 140:1497-1509, 1998.
28. Iavarone and Massague, Repression of the CDK activator Cdc25A and cell-cycle arrest by cytokine TGF-beta in cells lacking the CDK inhibitor p15. *Nature*, 387:417-22, 1997.
29. Pietenpol et al., TGF-β1 Inhibition of c-Myc transcription and growth in keratinocytes is abrogated by viral transforming protein with pRB binding domains. *Cell*, 61:777-85, 1990.
30. Neuman et al., Helix-loop-helix transcription factors regulate Id2 gene promoter activity. *FEBS Lett.*, 374:279-83, 1995.
31. Boyd et al., c-Myc target gene specificity is determined by a post-DNA-binding mechanism. *Proc. Natl. Acad. Sci. USA*, 95:13887-892, 1998.
32. Morrow et al., Overexpression of the Helix-Loop-Helix protein Id2 blocks T cell development at multiple stages. *Mol. Immunol.*, 36:491-503, 1999.
33. Florio et al., Id2 promotes apoptosis by a novel mechanism independent of dimerization to basic helix-loop-helix factors. *Mol. Cell. Biol.*, 18:5435-44, 1998.
34. Cooper et al., Expression of the Id family helix-loop-helix regulators during growth and development in the hematopoietic system. *Blood*, 89:3155-65, 1997.
35. Tsai et al., Mutation of E2f-1 suppresses apoptosis and inappropriate S phase entry and extends survival of Rb-deficient mouse embryos. *Mol. Cell*, 2:293-304, 1998.
36. Jen et al., Expression patterns of Id1, Id2, and Id3 are highly related but distinct from that of Id4 during mouse embryogenesis. *Dev. Dyn.*, 207:235-52, 1996.
37. Yokota et al., Development of peripheral lymphoid organs and natural killer cells depends on the helix-loop-helix inhibitor Id2. *Nature*, 397:702-06, 1999.
38. Lufkin et al., Homeotic transformation of the occipital bones of the skull by ectopic expression of a homeobox gene. *Nature*, 359:835-41, 1992.
39. Jacobs et al., The oncogene and Polycomb-group gene bmi-1 regulates cell proliferation and senescence through the ink4a locus. *Nature*, 397:164-68, 1999.
40. Serrano et al., Oncogenic ras provokes premature cell senescence associated with accumulation of p53 and p16INK4a. *Cell*, 88:593-602, 1997.
41. Iavarone and Massague, E2F and histone deacetylase mediate transforming growth factor beta repression of cdc25A during keratinocyte cell cycle arrest. *Mol. Cell. Biol.*, 19:916-22, 1999.
42. Biggs et al., A human Id-like helix-loop-helix protein expressed during early development. *Proc. Natl. Acad. Sci. USA*, 89:1512-16, 1992.
43. Wolfe et al., Symptoms and suffering at the end of life in children with cancer. *N. Engl. J. Med.*, 342(5):326-33, 2000.

44. Ross et al., Childhood cancer in the United States. A geographical analysis of cases from the Pediatric Cooperative Clinical Trials Groups. *Cancer*, 77(1):201-07, 1996.
45. Bunin et al., Increasing incidence of childhood cancer: report of 20 years experience from the greater Delaware Valley Pediatric Tumor Registry. *Paediatr. Perinat. Epidemiol.*, 10(3):319-38, 1996.
46. Kleef et al., The helix-loop-helix protein Id2 is overexpressed in human pancreatic cancer. *Cancer Res.*, 58(17): 3769-72, 1998.
47. Ishiguro et al., Id2 expression increases with differentiation of human myeloid cells. *Blood*, 78(12):5225-31, 1996.
48. Ishiguro et al., Expression of ID2 and ID3 mRNA in human lymphocytes. *Leuk. Res.*, 19(12):989-96, 1995.
49. Beers and Berkow, eds., *The Merck Manual of Diagnosis and Therapy*, 17th ed. (Whitehouse Station, N.J.: Merck Research Laboratories, 1999) 1442, 2364-66.
50. Linet et al., Cancer surveillance series: recent trends in childhood cancer incidence and mortality in the United States. *J. Natl. Cancer Inst.*, 91(12):1051-8, 1999.
51. Norton, J. D., ID helix-loop-helix proteins in cell growth, differentiation and tumorigenesis. *J. Cell Sci.*, 113:3897-905, 2000.
52. Lasorella et al., Id2 is a retinoblastoma protein target and mediates signalling by Myc oncoproteins. *Nature*, 407: 592-98, 2000.
53. Dyson, N., The regulation of E2F by pRB-family proteins. *Genes Dev.*, 12:2245-62, 1998.
54. Mulligan and Jacks, The retinoblastoma gene family: cousins with overlapping interests. *Trends Genet.*, 14:223-29, 1998.
55. Sellers and Kaelin, Role of the retinoblastoma protein in the pathogenesis of human cancer. *J. Clin. Oncol.*, 15:3301-12, 1997.
56. Chan et al., MYCN protein expression as a predictor of neuroblastoma prognosis. *Clin. Cancer Res.*, 3:1699-706, 1997.
57. Hirning et al., A comparative analysis of N-myc and c-myc expression and cellular proliferation in mouse organogenesis. *Mech. Dev.*, 33:119-25, 1991.
58. Bordow et al., Prognostic significance of MYCN oncogene expression in childhood neuroblastoma. *J. Clin. Oncol.*, 16:3286-94, 1998.
59. Hiyama et al., Immunohistochemical analysis of N-myc protein expression in neuroblastoma: correlation with prognosis of patients. *J. Pediatr. Surg.*, 26:838-43, 1991.
60. Paul et al., Stage IV neuroblastoma in infants. Long-term survival. *Cancer*, 67:1493-97, 1991.
61. Brodeur et al., Neuroblastoma. Effect of genetic factors on prognosis and treatment. *Cancer*, 70:1685-94, 1992.
62. Toma et al., Evidence that helix-loop-helix proteins collaborate with retinoblastoma tumor suppressor protein to regulate cortical neurogenesis. *J. Neurosci.*, 20:7648-56, 2000.
63. Lyden et al., Id1 and Id3 are required for neurogenesis, angiogenesis and vascularization of tumour xenografts. *Nature*, 401:670-77, 1999.
64. Cohn et al., MYCN expression is not prognostic of adverse outcome in advanced-stage neuroblastoma with nonamplified MYCN. *J. Clin. Oncol.*, 18:3604-13, 2000.
65. Cordon-Cardo et al., Altered expression of the retinoblastoma gene product: prognostic indicator in bladder cancer. *J. Natl. Cancer Inst.*, 84:1251-56, 1992.
66. Kratzke et al., Rb and p16INK4a expression in resected non-small cell lung tumors. *Cancer Res.*, 56:3415-20, 1996.
67. Cance et al., Altered expression of the retinoblastoma gene product in human sarcomas. *N. Engl. J. Med.*, 323: 1457-62, 1990.
68. Wang et al., A role for the helix-loop-helix protein Id2 in the control of oligodendrocyte development. *Neuron*, 29:603-14, 2001.
69. Mori et al., Lactation defect in mice lacking the helix-loop-helix inhibitor Id2. *Embo J.*, 19:5772-81, 2000.

All publications mentioned hereinabove are hereby incorporated in their entireties. While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for determining whether a subject with neuroblastoma has a stage I, stage II, stage III, or stage IV neuroblastoma, the method comprising:
   a) obtaining from a subject diagnosed with neuroblastoma a sample comprising neuroblastoma cells from a solid tumor; and
   b) detecting Id2 protein in intact cells in the sample using an antibody, or Fab or F(ab')$_2$ fragment thereof, that is reactive with Id2 protein,
   wherein a sample with an Id2 labeling index of about 5% of the cells in the sample indicates that the neuroblastoma is a stage I neuroblastoma;
   wherein a sample with an Id2 labeling index of about 30% of the cells in the sample indicates that the neuroblastoma is a stage II neuroblastoma;
   wherein a sample with an Id2 labeling index of about 35% of the cells in the sample indicates that the neuroblastoma is a stage III neuroblastoma; and
   wherein a sample with an Id2 labeling index of about 50% of the cells in the sample indicates that the neuroblastoma is a stage IV neuroblastoma.

2. The method of claim 1, wherein the antibody or fragment thereof is labeled with a detectable marker.

3. The method of claim 1, wherein the subject is a human.

4. The method of claim 1, wherein the subject is less than 1 year old.

5. A method for determining whether a subject with neuroblastoma has a stage IV neuroblastoma, the method comprising:
   a) obtaining from a subject diagnosed with neuroblastoma a sample comprising neuroblastoma cells from a solid tumor; and
   b) detecting Id2 protein in intact cells in the sample,
   wherein samples with detectable Id2 protein in the nuclei of 25% or more tumor cells are determined to be stage IV neuroblastoma.

6. The method of claim 5, wherein the subject is a human.

7. The method of claim 5, wherein the subject is less than 1 year old.

8. The method of claim 5, wherein the Id2 protein is detected using an antibody, or Fab or F(ab')$_2$ fragment thereof, that is reactive with Id2 protein, and the antibody or fragment thereof is labeled with a detectable marker.

9. A method for predicting survival in a subject with neuroblastoma, the method comprising:
   a) obtaining from a subject diagnosed with neuroblastoma a sample comprising neuroblastoma cells from a solid tumor;
   b) detecting Id2 protein in intact cells in the sample; and
   c) predicting survival of the subject;
   wherein subjects with sample cells positive for Id2 show decreased likelihood of survival compared to subjects with sample cells negative for Id2.

10. The method of claim 9, wherein subjects with sample cells positive for Id2 protein show a lower than 50% chance of survival at 20 months or more after diagnosis.

11. The method of claim 9, wherein subjects with sample cells negative for Id2 protein show a greater than 80% likelihood of survival at 20 months or more after diagnosis.

12. The method of claim 9, wherein the subject is a human.

13. The method of claim 9, wherein the subject is less than 1 year old.

14. The method of claim 9, wherein the Id2 protein is detected using an antibody, or Fab or F(ab')$_2$ fragment thereof, that is reactive with Id2 protein, and the antibody or fragment thereof is labeled with a detectable marker.

* * * * *

SEQUENCE LISTING

```
<160> NUMBER OF SEQ ID NOS: 6

<210> SEQ ID NO 1
<211> LENGTH: 405
<212> TYPE: DNA
<213> ORGANISM: Homo sapiens

<400> SEQUENCE: 1
atgaaagcct tcagtcccgt gaggtccgtt aggaaaaaca gcctgtcgga ccacagcctg      60
ggcatctccc ggagcaaaac ccctgtggac gacccgatga gcctgctata caacatgaac     120
gactgctact ccaagctcaa ggagctggtg cccagcatcc cccagaacaa gaaggtgagc     180
aagatggaaa tcctgcagca cctcatcgac tacatcttgg acctgcagat cgccctggac     240
tcgcatccca ctattgtcag cctgcatcac cagagacccg ggcagaacca gcgctccagg     300
acgccgctga ccaccctcaa cacggatatc agcatcctgt ccttgcaggc ttctgaattc     360
ccttctgagt taatgtcaaa tgacagcaaa gcactgtgtg gctga                     405
```

-continued

```
<210> SEQ ID NO 2
<211> LENGTH: 134
<212> TYPE: PRT
<213> ORGANISM: Homo sapiens

<400> SEQUENCE: 2

Met Lys Ala Phe Ser Pro Val Arg Ser Val Arg Lys Asn Ser Leu Ser
 1               5                  10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Ser Lys Met Glu Ile
    50                  55                  60

Leu Gln His Leu Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Arg Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Ala Leu Cys Gly
    130

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tctgttccac tgtggcacgt at                                            22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctcgataatg gggaaacagt gt                                            22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aggctttcat gctgaccgc                                                19

<210> SEQ ID NO 6
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 6
gcgagttgtc gcacggtct                                                    19
```